(12) United States Patent
Schulz et al.

(10) Patent No.: US 6,339,179 B1
(45) Date of Patent: *Jan. 15, 2002

(54) PRODUCTION OF ALKYL AROMATICS BY PASSING TRANSALKYLATION EFFLUENT TO ALKYLATION ZONE AND TO PRODUCT RECOVERY ZONE

(75) Inventors: Russell C. Schulz, Glen Ellyn; Gregory J. Gajda; Guy B. Woodle, both of Mount Prospect; Andrew S. Zarchy, Kildeer, all of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/625,707

(22) Filed: Jul. 25, 2000

Related U.S. Application Data

(63) Continuation-in-part of application No. 09/124,205, filed on Jul. 28, 1998, now Pat. No. 6,096,935.
(60) Provisional application No. 60/053,905, filed on Jul. 28, 1997.

(51) Int. Cl.[7] .............................. C07C 2/58; C07C 2/66; C07C 15/067
(52) U.S. Cl. ........................ 585/323; 585/315; 585/316; 585/313; 585/312; 585/314; 585/310; 585/319; 585/320; 585/449; 585/450; 585/475; 585/467
(58) Field of Search ................................. 585/310, 312, 585/313, 314, 315, 316, 319, 320, 323, 449, 450, 475, 467

(56) References Cited

U.S. PATENT DOCUMENTS

| | | |
|---|---|---|
| 4,008,290 A | 2/1977 | Ward ........................... 585/314 |
| 4,051,191 A | 9/1977 | Ward ........................... 585/450 |
| 4,083,886 A | 4/1978 | Michalko ..................... 585/475 |
| 4,587,370 A | 5/1986 | DeGraff ....................... 585/450 |
| 4,695,665 A | 9/1987 | DeGraff ....................... 585/450 |
| 4,891,458 A | 1/1990 | Innes et al. .................. 585/323 |
| 4,922,053 A | 5/1990 | Waguespack et al. ........ 585/449 |
| 5,003,119 A | 3/1991 | Sardina et al. .............. 585/323 |
| 5,030,786 A | 7/1991 | Shamshoum et al. ....... 585/467 |
| 5,177,285 A | 1/1993 | Van Opdorp et al. ....... 585/467 |
| 5,336,821 A | 8/1994 | DeGraff et al. ............. 585/402 |
| 5,723,710 A | 3/1998 | Gajda et al. ................. 585/467 |
| 5,902,917 A | 5/1999 | Collins et al. .............. 585/323 |
| 5,998,684 A | 12/1999 | Ho et al. ..................... 585/323 |
| 6,096,935 A | * 8/2000 | Schulz et al. ............... 585/323 |

FOREIGN PATENT DOCUMENTS

EP    0 733 608 A1    9/1996

* cited by examiner

Primary Examiner—Thuan D. Dang
(74) Attorney, Agent, or Firm—John G. Tolomei; John F. Spears, Jr.; Michael A. Moore

(57) ABSTRACT

A process for producing alkyl aromatics using a transalkylation reaction zone and an alkylation reaction zone is disclosed. One portion of the transalkylation reaction zone effluent passes to an alkylation reaction zone where an aromatic substrate is alkylated to the desired alkyl aromatic. At least a portion of the alkylation reaction zone effluent and another portion of the transalkylation reaction zone effluent pass to a product recovery zone. This process decreases the capital and operating costs of recycling aromatic substrate to the transalkylation and/or alkylation reaction zone while maintaining operational flexibility. This process is well suited for solid transalkylation and alkylation catalysts. Ethylbenzene and cumene may be produced by this process.

27 Claims, 4 Drawing Sheets

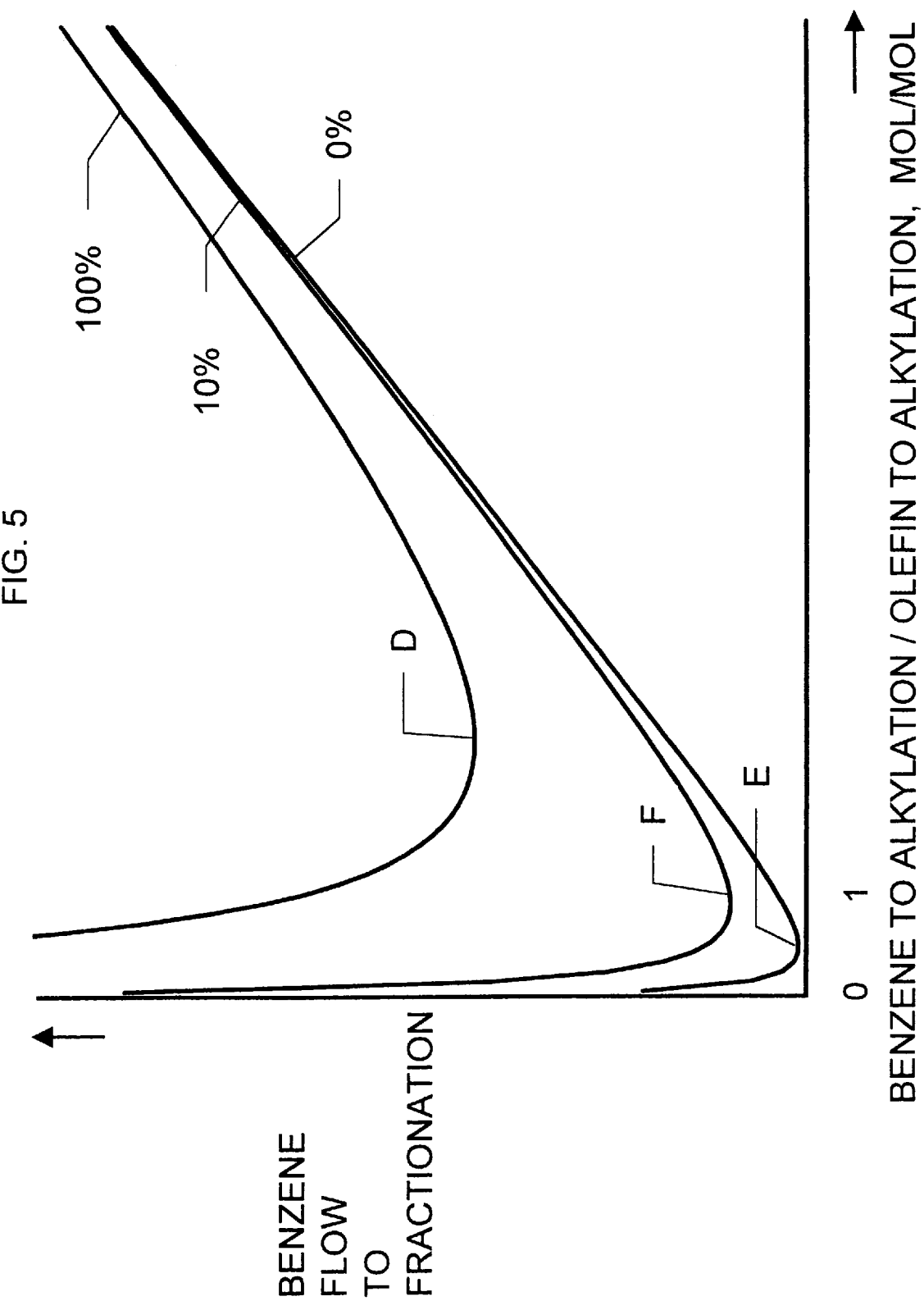

PRODUCTION OF ALKYL AROMATICS BY PASSING TRANSALKYLATION EFFLUENT TO ALKYLATION ZONE AND TO PRODUCT RECOVERY ZONE

CROSS-REFERENCE TO RELATED APPLICATION

This application is a continuation-in-part application of U.S. patent application Ser. No. 09/124,205, filed Jul. 28, 1998 now U.S. Pat. No. 6,096,935 which claims benefit of Ser. No. 60/053,905 filed on Jul. 28, 1997.

FIELD OF THE INVENTION

This invention relates to a hydrocarbon conversion process. The invention more specifically relates to the production of alkylaromatic hydrocarbons by the reaction of an acyclic olefinic hydrocarbon with an aromatic substrate hydrocarbon.

BACKGROUND OF THE INVENTION

The alkylation of aromatic substrates with olefins to produce monoalkyl aromatics is a well developed art which is practiced commercially in large industrial units. One commercial application of this process is the alkylation of benzene with ethylene to produce ethylbenzene which is subsequently used to produce styrene. Another application is the alkylation of benzene with propylene to form cumene (isopropylbenzene) which is subsequently used in the production of phenol and acetone. Those skilled in the art are therefore familiar with the general design and operation of such alkylation processes.

The performances of alkylation processes for producing monoalkyl aromatics are influenced by the stability and activity of the solid catalyst at the operating conditions of the process. For example, as the molar ratio of aromatic substrate per olefin increases, currently available catalysts typically exhibit an improved selectivity to the monoalkyl aromatic. But even at a high molar ratio of aromatic substrate per olefin, several polyalkyl aromatic by-products such as dialkyl aromatics and trialkyl aromatics accompany monoalkyl aromatic production.

Although the formation of dialkyl and trialkyl aromatics might, at first glance, be viewed as by-products that represent a reduction in the efficient use of the olefin, in fact each can be readily transalkylated with the aromatic substrate using a transalkylation catalyst to produce the monoalkyl aromatic. So-called combination processes combine an alkylation zone with a transalkylation zone in order to maximize monoalkyl aromatic production.

One disadvantage of combination processes is that separate reaction zones for alkylation and for transalkylation duplicate costly equipment. Each reaction zone requires what amounts to its own reaction train, including separate and independent reaction vessels, heaters, heat exchangers, piping, and instrumentation.

Another disadvantage of combination processes is the great expense associated with recovering and recycling unreacted aromatic substrate from the effluents of the alkylation and transalkylation reaction zones. Alkylation reaction zones generally operate at a molar ratio of aromatic substrate per alkylation agent that is at least 1:1 in order to help ensure a high selectivity toward the monoalkyl aromatic. Transalkylation reaction zones generally operate at a molar ratio of aromatic per dialkyl aromatic that is much greater than the stoichiometric ratio of 1:1 in order to help ensure a high conversion of the dialkyl aromatic to the monoalkyl aromatic. Consequently, the alkylation and transalkylation reaction zone effluents contain a significant quantity of unreacted aromatic substrate, which must be removed in order to obtain the monoalkyl aromatic product and which must be recycled in order to ensure the efficient use of the aromatic substrate.

Prior art combination processes lessen the great expense incurred in removing and recycling the unreacted aromatic substrate contained in the alkylation and transalkylation reaction zone effluents by three methods. One method is to pass the alkylation effluent stream and the transalkylation effluent stream to a single, common product recovery facility, in which the same distillation columns remove unreacted aromatic from both effluent streams and recycle unreacted aromatic substrate to both reaction zones. In this method, the respective flows through alkylation and transalkylation can be considered to be in parallel. Incidentally, a no less important function of these distillation columns in the prior art is the removal of polyalkyl aromatics other than dialkyl and trialkyl aromatics and of other heavy alkylation and transalkylation by-products such as diphenylalkanes, which are collectively referred to herein as heavies. Although sharing common product equipment in this manner reduces the capital expense of a combination process, the energy requirements for vaporizing and condensing the aromatic substrate from the effluent streams remains undiminished.

A second method is to pass the entire transalkylation effluent stream to the alkylation zone and then to pass the alkylation effluent stream to the product recovery facility. In this method, the flow through alkylation and transalkylation can be considered as being in series, with transalkylation upstream of alkylation. This arrangement is sometimes referred to as a "cascaded" flow scheme, with transalkylation leading alkylation. The advantage of this method is that unreacted aromatic substrate in the transalkylation effluent stream is directly used in alkylation without expending energy to separate the aromatic substrate from monoalkyl and polyalkyl aromatics. However, an upset condition or any other disruption in the operation of the transalkylation zone propagates directly to the alkylation zone, which can disrupt or adversely affect alkylation reactions. Moreover, even if the transalkylation zone is operating at optimum transalkylation conditions, its effluent may not be an optimum feed stream for the alkylation zone.

A typical scenario helps illustrate the susceptibility to transalkylation upsets of alkylation zones in a cascaded flow scheme with transalkylation leading alkylation. It is well known that the performance of transalkylation catalysts can be affected by the concentration of water in the transalkylation reactor. An unexpected ingress of an excessive amount of water into the transalkylation reactor can cause the conversion of polyalkyl aromatics to monoalkyl aromatics to drop precipitously, say from 70% to 50%. When this occurs in a commercial combination process, levels of polyalkyl aromatics begin to accumulate within the product recovery facility, and in response operators increase the flow rate of polyalkyl aromatics to the transalkylation reactor by 40%. In a cascaded flow scheme with transalkylation leading alkylation, this necessarily increases the flow rate of transalkylation effluent, and especially of polyalkyl aromatics, to the alkylation reactor by 40%. There, the polyalkyl aromatics tend to be further alkylated by olefin, which produces even more highly alkylated polyalkyl aromatics that must be converted in transalkylation. Thus, passing transalkylation effluent to alkylation propagates the initial upset from transalkylation to alkylation and destabilizes the entire combination process. This compounding and prolongation of the initial disturbance can necessitate reducing alkylation throughput and lead to significant economic losses.

A third method is to pass the entire alkylation effluent stream to the transalkylation zone and then to pass the transalkylation effluent stream to the product recovery facility. Like the second method, the flow through alkylation and transalkylation can be considered as being in series, but in this method alkylation is upstream of transalkylation. This arrangement is sometimes referred to as a "cascaded" flow scheme, with alkylation leading transalkylation. Although this method does not expend energy separating unreacted aromatic substrate from the alkylation effluent stream, passing alkylation effluent to transalkylation significantly decreases the yield of the desired monoalkyl aromatic product.

Thus, the high utilities expenses of combination processes as well as the costly duplication of reaction zones has given impetus to research with a goal of minimizing energy requirements and of integrating the alkylation and transalkylation zones efficiently and economically.

SUMMARY OF THE INVENTION

This invention is an economical and efficient combination process for producing an alkyl aromatic by alkylation and by transalkylation. In this invention, one portion of the transalkylation zone effluent stream passes to the alkylation zone, another portion of the transalkylation zone effluent stream passes to the product recovery zone, and the alkylation zone effluent stream also passes to the product recovery zone. Thus, the second portion, but not the first portion, of the transalkylation effluent stream bypasses the alkylation zone. The primary advantage of this invention is that it minimizes the flow of unreacted aromatic substrate to the product recovery zone. For example, in comparison with prior art processes that pass each of the entire transalkylation effluent stream and the entire alkylation effluent stream in parallel to the product recovery zone, this invention decreases the flow of unreacted aromatic substrate to the product recovery zone for a given ratio of aromatic substrate per olefin in the alkylation zone.

Another important advantage of this invention is apparent when this invention is compared to prior art processes that pass the entire transalkylation effluent to the alkylation zone and then pass the alkylation effluent stream to the product recovery zone. This invention allows the alkylation zone to operate with an additional degree of freedom for a given flow rate of unreacted aromatic substrate to the product recovery zone. This additional degree of freedom allows the feed to the transalkylation zone to be adjusted over a wide range of flow rates as necessary to achieve the required conversion of polyalkyl aromatic to monoalkyl aromatic, regardless of the alkylation feed rate or without having an adverse impact on alkylation conditions. For example, this invention avoids the need to increase the alkylation feed rate in response to an unexpected upward spike in the water concentration in the transalkylation reaction zone, even if the transalkylation feed rate is increased. Using this invention, transalkylation effluent in excess of the desired alkylation feed rate can bypass the alkylation reaction zone and pass directly to the product recovery facility. Thus, this invention helps to mitigate, rather than to aggravate, upsets in transalkylation and improves the profitability of combination processes.

The present invention minimizes the flow of aromatic substrate to the product recovery facility of a commercial combination process over a broad range of operating conditions. At these same conditions, the prior art combination processes are incapable of minimizing the flow of aromatic substrate to the product recovery facility. The minimum flow rate of aromatic substrate to the product recovery facility is apparent from an x-y chart in which the y-axis is the flow rate of aromatic substrate to the product recovery facility and the x-axis is the molar ratio of aromatic substrate per alkylating agent in the alkylation zone. Although the exact shape of the curve plotted on such a chart depends on the operating conditions for the alkylation and transalkylation zones, a typical curve that is representative of a the curves for a broad range of commercial operating conditions has a characteristic concave-upward shape. There is an optimum molar ratio for which the flow rate of the aromatic substrate is a minimum. At molar ratios greater than the optimum, the flow rate of aromatic substrate is greater than the minimum, because the aromatic substrate content in the alkylation effluent is high. At molar ratios less than the optimum, a high amount of aromatic substrate is present in the transalkylation effluent, since a large amount of aromatic substrate must be supplied to transalkylation in order to compensate for polyalkylation in alkylation, and so the flow rate of aromatic substrate to the product recovery facility is greater than the minimum. Unlike the prior art combination processes, the present invention provides the flexibility to operate at this optimum molar ratio over a wide range of operating conditions.

It is now recognized that the curve on the x-y chart described in the previous paragraph itself is a function of the fraction of the transalkylation effluent that passes directly to the product recovery facility. For example, when the entire transalkylation effluent passes directly to the product recovery facility, the curve is shifted upward and towards the right on the x-y chart, so that the minimum flow rate of aromatic substrate increases and the optimum molar ratio increases also. This is the position of the curve on the x-y chart for the prior art processes where the transalkylation and alkylation effluents flow in parallel to the product recovery facility. However, for such a process the minimum flow rate of aromatic substrate to the product recovery facility is so high that the process is not economical because the capital and operating costs associated with recycling aromatic substrate are prohibitive. On the other hand, when none of the transalkylation effluent passes directly to the product recovery facility, the curve is shifted downward and towards the left on the x-y chart, so that the minimum flow rate of aromatic substrate and the optimum molar ratio both decrease. The curve on the x-y chart is in this position for the cascaded prior art processes where transalkylation leads alkylation and the entire transalkylation effluent flows in series to the alkylation zone. However, for such a process the optimum molar ratio is so low (e.g., below 1:1), that it is impractical to use the combination process for monoalkylation, since alkylation at extremely low molar ratios produces an unacceptable yield of polyalkyl aromatics byproducts.

The present invention solves the dilemma that is presented by the unacceptable alternatives of the prior art processes. The present invention passes one portion of the transalkylation effluent stream to the alkylation zone and another portion of the transalkylation effluent stream to the product recovery facilities. Therefore, the present invention is capable of operating at minimum flow rates of aromatic substrate to the product recovery facilities that are economical and at optimum molar ratios of aromatic substrate per alkylating agent in alkylation that are practical and suitable for monoalkylation. In addition, the present invention provides an extra degree of operating flexibility that allows the feed rate to the transalkylation zone to be adjusted independently of the feed rate to the alkylation zone. In the event of a water upset or other disturbance in transalkylation, the combination process of this invention can be readily adjusted to rapidly reestablish normal operating conditions.

The costs associated with recycling the alkylation substrate can be decreased by diverting to the transalkylation reaction zone some or all of the alkylation substrate that passes directly to the alkylation reaction zone in some prior art processes. Because diverting this benzene to the transalkylation reaction zone increases conversion of polyalkyl aromatics in the transalkylation reaction zone, the alkylation reaction zone may be operated with less alkylation substrate being passed directly to the alkylation reaction zone. Thus, less excess alkylation substrate is present in the alkylation effluent stream and, therefore, less capital and utilities need to be spent to recover the desired alkylaromatic product from the excess alkylation substrate in the alkylation effluent stream. Consequently, this invention can be operated in a manner that vaporizes, condenses, and recycles a decreased quantity not only of polyalkyl aromatics but also of excess alkylation substrate. Additional cost savings may be attainable with this invention by consolidating the alkylation and transalkylation reaction zones into a single reactor vessel, and by eliminating in whole or in part recycling of the alkylation effluent stream, if any, to the alkylation reaction zone. Thus, in summary, a combination process that uses this invention can operate with significantly lower capital and utility costs compared to a prior art combination process.

Combination processes that will benefit most from this invention include those in which passing the transalkylation reactor effluent to the alkylation reaction zone does not have significant adverse effects on the production of monoalkyl aromatic in the alkylation zone or on the deactivation rate of the alkylation catalyst. For this reason, this invention is particularly applicable to combination processes that use beta zeolite as the alkylation catalyst, because at alkylation conditions beta zeolite produces nearly the equilibrium amount of monoalkyl aromatic and because, surprisingly, beta zeolite is not rapidly deactivated by polyalkyl aromatics in the alkylation feed. This invention is also particularly applicable to those combination processes that benefit from operation at a relatively high molar ratio of phenyl groups per alkyl group in the transalkylation reaction zone and a relatively low molar ratio of aromatic per alkyl group in the alkylation reaction zone.

A broad objective of this invention is to provide an improved combination process for the production of alkyl aromatics that minimizes the capital and operating expenses associated with recycling aromatic substrate feedstock. Another objective is to provide a combination process for the production of alkyl aromatics in which, when upsets in the transalkylation zone occur, such upsets are prevented from propagating to the alkylation zone, stable operation of the process is maintained, and normal operation of the process is reestablished expeditiously.

In a broad embodiment, this invention is a process for producing alkyl aromatic hydrocarbons. A first transalkylation feed stream comprising an aromatic substrate hydrocarbon passes to a transalkylation reaction zone. A second transalkylation feed stream comprising a first alkyl aromatic hydrocarbon having more than one alkyl group passes to the transalkylation reaction zone. In the transalkylation zone, the aromatic substrate hydrocarbon transalkylates with the first alkyl aromatic hydrocarbon in the presence of a first solid catalyst. The transalkylation reaction produces a second alkyl aromatic hydrocarbon having at least one more alkyl group than the aromatic substrate hydrocarbon. A transalkylation effluent stream comprising the aromatic substrate hydrocarbon and the second alkyl aromatic hydrocarbon is recovered from the transalkylation reaction zone. A first alkylation feed stream comprising an alkylating agent passes to an alkylation reaction zone. A first aliquot portion of the transalkylation effluent stream passes to the alkylation reaction zone. In the alkylation zone, the aromatic substrate hydrocarbon alkylates with the alkylating agent in the presence of a second solid catalyst to produce an alkylation effluent stream comprising the second alkyl aromatic hydrocarbon. At least a portion of the alkylation effluent stream and a second aliquot portion of the transalkylation effluent stream pass to a product separation zone. In the product separation zone, the entering compounds are separated into a product stream comprising the second alkyl aromatic hydrocarbon, a first recycle stream comprising the aromatic substrate, and a second recycle stream comprising the first alkyl aromatic hydrocarbon. At least a portion of the first transalkylation feed stream is formed from at least a portion of the first recycle stream. At least a portion of the second transalkylation feed stream is formed from at least a portion of the second recycle stream.

Other objectives and embodiments of this invention are disclosed in the detailed description.

Information Disclosure

Prior art alkylation processes are well described in the literature.

U.S. Pat. No. 4,051,191 describes catalysts, reaction conditions, and a separation method for the recovery of cumene that uses a rectification zone and a two-column fractionation train.

U.S. Pat. Nos. 4,695,665 and 4,587,370 are particularly directed to the separation of products and the recovery of recycle streams from processes for the alkylation of aromatic hydrocarbons, and U.S. Pat. No. 4,695,665 discloses the use of a flash drum in combination with an effluent rectifier to recover unreacted feed components.

U.S. Pat. No. 4,891,458 describes the use of beta zeolite for the alkylation of aromatic hydrocarbons with alkenes to produce alkyl aromatics. U.S. Pat. No. 4,891,458 also discloses that transalkylation can occur in an alkylation reactor, and that additional monoalkyl aromatic hydrocarbons can be produced in an alkylation reactor by recycling polyalkyl aromatic hydrocarbons to the alkylation reactor to undergo transalkylation.

U.S. Pat. No. 4,922,053 describes a process for alkylating benzene with ethylene in a multibed reactor wherein polyethylbenzenes are recycled to the first alkylation bed and also to one or more of the other alkylation beds in order to increase ethylbenzene yield.

U.S. Pat. No. 5,030,786 discloses an alkylation process wherein the feed stream is dehydrated to enhance the performance of beta or Y zeolites in the alkylation process.

U.S. Pat. No. 5,336,821 describes the use of beta zeolite for the alkylation of aromatic hydrocarbons in a process that is improved by an indirect heat exchanger to recover the heat of reaction. In one embodiment, the alkylation reactor effluent passes through the heat exchanger and is recycled to the alkylation reactor.

Prior art transalkylation processes are well described in the literature. U.S. Pat. No. 4,083,886 describes a process for the transalkylation of the alkyl aromatic hydrocarbons that uses a zeolitic catalyst. U.S. Pat. No. 4,891,458 describes the use of beta zeolite for the transalkylation of aromatic hydrocarbons with polyalkyl aromatic hydrocarbons. European Patent Application EP 0 733 608 A1 discloses the use of an alumina silicate catalyst having an average crystal size of less than about 0.5 microns for the transalkylation of polyalkyl benzenes with benzene in a reaction zone with an alkylating agent such as ethylene.

Combination processes that produce alkyl aromatic products by using an alkylation reaction zone and a transalkylation reaction zone are also well known.

U.S. Pat. No. 4,008,290 describes a combination process in which the alkylation effluent and the transalkylation effluent are passed to a common separation zone, which separates the two effluents into product, by-product, and recycle streams including a recycle benzene stream. A portion of the alkylation effluent is recycled to the alkylation reaction zone in order to decrease the portion of the recycle benzene stream that is recycled to the alkylation reaction zone.

U.S. Pat. No. 5,003,119 describes a combination process for producing monoalkyl aromatics in which the alkylation effluent passes to the transalkylation reaction zone, and the transalkylation effluent passes to a separation zone. U.S. Pat. No. 5,003,119 also describes passing dialkyl aromatics to the alkylation reaction zone.

U.S. Pat. No. 5,177,285 discloses an alkylation process that is improved by maintaining the feed to the alkylation zone in a relatively wet condition and the feed to the transalkylation zone in a relatively dry condition. The process operates with a relatively pure ethylene feed as an alkylating agent with a large excess of benzene.

U.S. Pat. No. 5,723,710 describes a surface-modified zeolite beta which exhibits stability and long catalyst life when used in alkylation and transalkylation of aromatic compounds. The teachings of U.S. Pat. No. 5,723,710 are incorporated herein by reference.

U.S. Pat. No. 5,902,917 describes a process for producing alkylaromatics, especially ethylbenzene and cumene, wherein a feedstock is first fed to a transalkylation zone and the entire effluent from the transalkylation zone is then cascaded directly into an alkylation zone along with an olefin alkylating agent, especially ethylene or propylene.

U.S. Pat. No. 5,998,684 describes a process for producing alkylaromatics that operates with an alkylation zone and a transalkylation zone, where the transalkylation zone and the alkylation zone are arranged for series flow and the transalkylation zone effluent is passed with an aromatic containing feed and the olefinic feed, which is preferably propylene or ethylene, to the alkylation zone.

BRIEF DESCRIPTION OF THE DRAWINGS

FIGS. 4 and 5 are x-y charts that illustrate the benefits of this invention relative to the prior art processes.

DETAILED DESCRIPTION OF THE INVENTION

Figure 1:
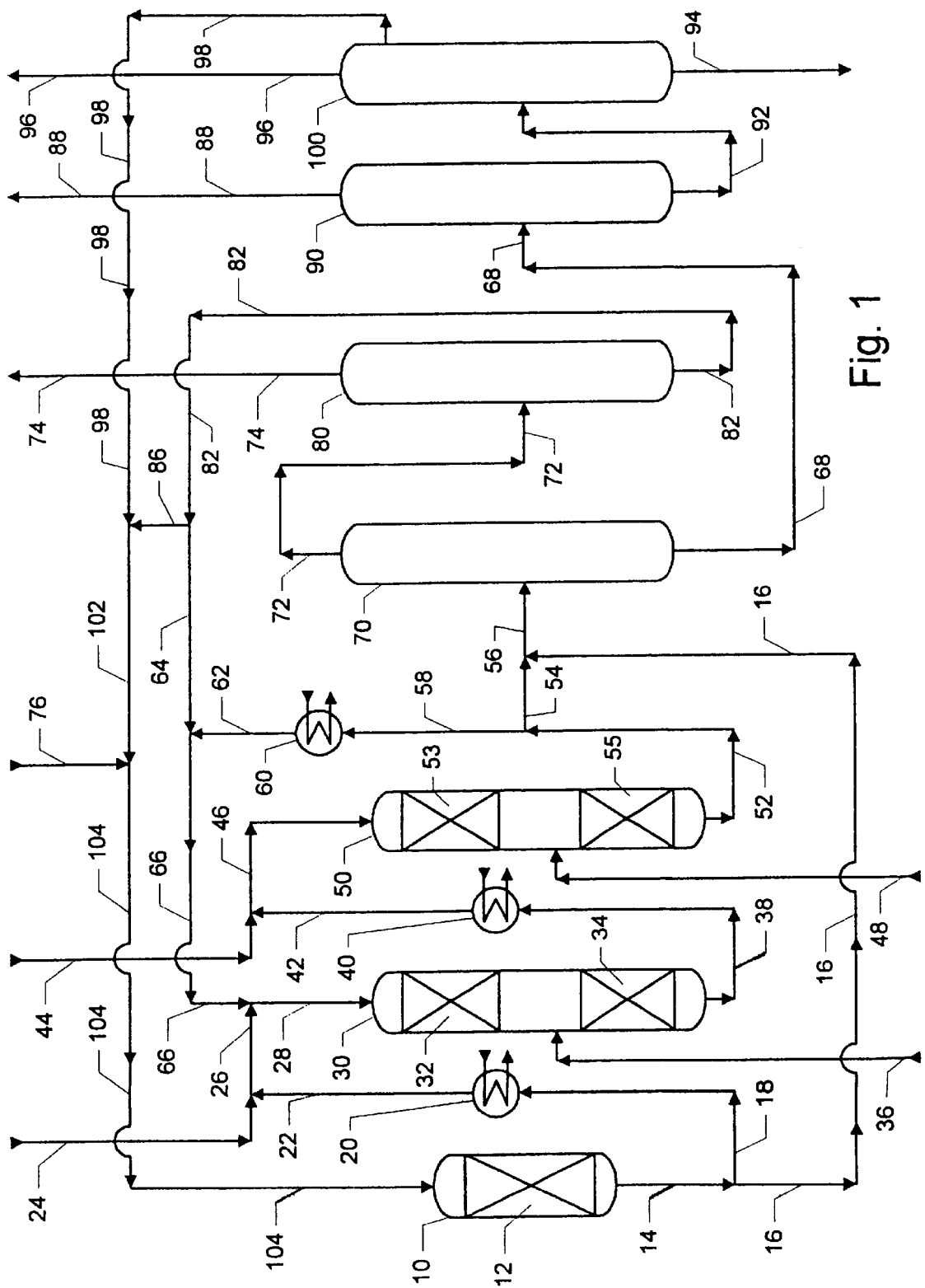
FIG. 1 is a schematic illustration of an embodiment of the invention.

This invention is suitable generally for alkylation substrates and alkylation agents, and more specifically to aromatic alkylation substrates and olefinic alkylating agents.

Benzene is the aromatic alkylation substrate of principal interest, but alkyl-substituted benzenes may be used. More than one aromatic alkylation substrate may be used. Monoolefins are the principal olefinic alkylating agent, but other diolefins, polyolefins, acetylene hydrocarbons, and substituted hydrocarbons can be used. The olefinic alkylating agent preferably contains 2 or 3 carbon atoms, but olefins having from 2 to 20 carbon atoms may be used. Ethylene or propylene is the preferred olefinic alkylating agent. More than one olefin may be used.

In addition to alkylation substrates and alkylation agents, this invention may also be suitable for transalkylation agents. The transalkylation agent transalkylates with the alkylation substrate to produce the desired product, namely the product of alkylating the alkylation substrate with the alkylating agent. The transalkylation agent may be introduced to the present invention via a feed from a source that is external to the present invention, but more commonly the transalkylation agent is a by-product of alkylating the alkylation substrate with the alkylating agent in the process that uses the present invention. Where the transalkylation agent is such an alkylation by-product, a transalkylation agent from an external source may not be needed, and the transalkylation agent can be passed to the transalkylation zone by recovering the transalkylation agent from the alkylation effluent stream and passing a stream enriched in transalkylation agent and depleted in desired product to the transalkylation reaction zone. Alternately and less preferably, some of the alkylation effluent stream may be passed without separation to the transalkylation reaction zone. This invention is suitable specifically for aromatic transalkylation agents having more than one alkyl (e.g., ethyl or propyl) group, and dialkyl benzenes are the principal aromatic transalkylation agents for producing monoalkyl benzenes. As the number of alkyl groups on the desired aromatic product increases, the number of alkyl groups on the principal aromatic transalkylation agent increases.

Generally, the alkylation substrate, alkylation agent, and transalkylation agent are hydrocarbons. As used herein, the term "hydrocarbon" means a compound that contains carbon and hydrogen and that may contain other atoms as well, such as halogens (e.g., fluorine, chlorine, and bromine), oxygen, sulfur, and nitrogen. These other atoms may be present, for example, in substituent groups that are substituted on the aromatic ring of an aromatic alkylation substrate or of an aromatic transalkylation agent.

The desired alkyl aromatic product has at least one more alkyl group than the aromatic substrate. One of the widely practiced hydrocarbon conversion processes to which this invention is applicable is the production of cumene by alkylation of benzene with propylene and by transalkylation of benzene with polyisopropylbenzenes that are alkylation by-products. Therefore, the discussion herein of this invention refers mainly to cumene processes. For the sake of clarity, the discussion herein of cumene transalkylation precedes that of cumene alkylation because an essential element of this invention is passing some transalkylation effluent to the alkylation zone. It is not intended that this discussion limit the scope of this invention as set forth in the claims.

In the transalkylation reaction zone, diisopropylbenzene and higher polyisopropylbenzenes transalkylate with benzene to produce cumene (isopropylbenzene). Generally, a catalyst promotes the transalkylation in the transalkylation reaction zone. The transalkylation catalyst for the present invention may be one of a class of aluminosilicate molecular sieves known as zeolites. The zeolitic molecular sieves suitable for use in the present invention are crystalline aluminosilicates which in the calcined form may be represented by the general formula:

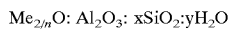

where Me is a cation, n is the valence of the cation, x has a value of from about 5 to 100, and y has a value of from about 2 to 10. Detailed descriptions of zeolites may be found in D. W. Breck, *Zeolite Molecular Sieves*, John Wiley and Sons, New York 1974, and in other standard references. Suitable zeolites for the transalkylation catalyst include zeolite Y, zeolite beta, ZSM-5, PSH-3, MCM-22, MCM-36, MCM49, and MCM-56. In general, each of the zeolites described hereinafter as suitable for the alkylation catalyst is suitable for the transalkylation catalyst. A preferred zeolite Y for transalkylation is essentially free of residual non-$H^+$ cations, by which it is meant that the non-$H^+$ cation content of the zeolite Y is less than 200 wppm calculated as $NH_3$ equivalents. A preferred zeolite for the transalkylation catalyst is zeolite beta as disclosed in U.S. Pat. Nos. 4,891,458 and 5,081,323, the teachings of which are incorporated herein by reference. Another preferred zeolite beta is the surface-modified zeolite beta that is described hereinafter and which is disclosed in U.S. Pat. No. 5,723,710, the teachings of which are incorporated herein by reference. The zeolite is generally present in an amount of at least 50 wt-% of the catalyst and more preferably in an amount of at least 90 wt-% of the catalyst. In most cases, the balance of the transalkylation catalyst other than the zeolite is a refractory inorganic oxide binder. The preferred inorganic oxide is alumina, with gamma-alumina, eta-alumina, and mixtures thereof being particularly preferred. Where the catalyst comprises a zeolite and an inorganic oxide, the zeolite content may be from 5 to 99 wt-% of the catalyst, and the inorganic oxide may be from 1 to 95 wt-% of the catalyst. Preferred transalkylation catalysts are zeolite Y with an alumina or silica binder and zeolite beta with an alumina or silica binder.

The transalkylation reaction can be carried out in a broad range of operating conditions that result in a high conversion of diisopropylbenzene (DIPB) to cumene. DIPB conversion is limited by equilibrium governed mainly by the ratio of phenyl groups per alkyl group and is generally greater than 30% and preferably greater than 50%. Operating conditions generally include a temperature of from about 210° F. (99° C.) to about the critical temperature of the alkylation substrate, which is about 554° F. (290° C.) for benzene and may be 889° F. (475° C.) or even higher for heavier alkylation substrates. The operating temperature is preferably from about 250 to about 350° F. (121 to 177° C.) for cumene production, and from about 340 to about 500° F. (171 to 260° C.) for ethylbenzene production, or encompassing from about 250 to about 500° F. (121 to 260° C.). The transalkylation pressure would generally be from 1 to about 130 atmospheres, but set so that the reactants are generally at least partially in the liquid phase and preferably in the liquid phase. Accordingly, the preferred pressure for the transalkylation reaction zone range is from 10 to about 50 atmospheres. A total liquid hourly space velocity (LHSV) of from 0.5 to 50 $hr^{-1}$ is desirable, with 0.5 to 5 $hr^{-1}$ being preferred. As used herein, the abbreviation "LHSV" means liquid hourly space velocity, which is defined as the volumetric flow rate of liquid per hour divided by the catalyst volume, where the liquid volume and the catalyst volume are in the same volumetric units. The water concentration is typically less than 200 wppm, and preferably less than 20 wppm, and more preferably less than 5 wppm.

The molar ratio of phenyl groups per alkyl group, which is often referred to as the phenyl/alkyl ratio, is a key operating variable for transalkylation because the equilibrium conversion of polyalkyl aromatics is a function of the phenyl/alkyl ratio. The numerator of this ratio is the number of moles of phenyl groups passing through the transalkylation zone during a specified period of time. The number of moles of phenyl groups is the sum of all phenyl groups, regardless of the compound in which the phenyl group happens to be. In the context of cumene production, for example, one mole of benzene, one mole of cumene, one mole of diisopropylbenzene (DIPB), and one mole of triisopropylbenzene (TIPB) each contribute one mole of phenyl group to the sum of phenyl groups. The denominator of this ratio is the number of moles of alkyl groups passing through the transalkylation zone during the same specified period of time. The number of moles of alkyl groups is the sum of all alkyl and alkenyl groups, regardless of the compound in which the alkyl or alkenyl group happens to be, except that paraffins are not included. Thus, in the production of cumene (isopropylbenzene), the number of moles of propyl groups is the sum of all propyl and propenyl groups, regardless of the compound in which the propyl or propenyl group happens to be, but excluding paraffins. Paraffins, such as propane, n-butane, isobutane, pentanes, and higher paraffins, are excluded from the computation of the number of moles of propyl groups. For example, one mole of propylene and one mole of cumene each contribute one mole of propyl group to the sum of propyl groups, whereas one mole of DIPB contributes two moles of propyl groups and one mole of TIPB contributes three moles of propyl groups. For cumene production, the phenyl/propyl ratio is generally from about 8:1 to about 1:1, and preferably from about 6:1 to about 3:1. Where the transalkylation feed consists of only benzene and DIPB, the phenyl/propyl ratio may be computed from the molar ratio of benzene per DIPB, which is referred to as the benzene/DIPB ratio, by using the mathematical formula, phenyl/propyl ratio=1/2×(benzene/DIPB ratio+1). This mathematical formula is sufficiently accurate as an approximation of the phenyl/propyl ratio when the cumene content or the TIPB content of the transalkylation feed is less than 1.0 vol.-%. The molar ratio of aromatic substrate per transalkylation agent is generally from about 13:1 to about 3:1. For ethylbenzene production, the phenyl/ethyl ratio is generally from about 10:1 to about 1:1, and preferably from about 7:1 to about 2:1.

The transalkylation reaction zone may be operated and arranged in any manner that provides the desired operating conditions and the required contacting of reactants and catalyst. A single contacting stage in transalkylation is routinely used, in part because the transalkylation reactions are neither very exothermic nor very endothermic.

The transalkylation effluent stream contains not only the desired monoalkyl aromatic product (cumene) but also unreacted transalkylation reactants as well as transalkylation by-products. Of the transalkylation reactants, benzene is usually the most abundant, because in transalkylation benzene is generally present in a stoichiometric excess to the polyisopropylbenzenes. Diisopropylbenzenes (DIPB) in the transalkylation feed also are generally present in the transalkylation effluent stream because the DIPB conversion in transalkylation is limited by equilibrium to less than 100%. Higher polyalkylbenzenes such as triisopropylbenzenes (TIPB) and tetraisopropyl-benzenes also may be present in the transalkylation effluent, either as an unreacted transalkylation reactant or as a transalkylation by-product from the reaction of a polyalkylbenzene with another polyalkylbenzene rather than with benzene. Even pentaisopropylbenzene, hexaisopropylbenzene, and diphenylpropanes may be present in the transalkylation effluent, although the concentrations of these components in the transalkylation effluent are usually low.

As mentioned previously, passing some of the transalkylation effluent stream to the alkylation reaction zone is an essential element of this invention. The portion of the transalkylation effluent stream that passes to the alkylation reaction zone is generally from about 0.5 to about 99.5%, commonly from about 25 to about 95%, and more commonly from about 50 to about 90%, of the transalkylation effluent stream. The portion of the transalkylation effluent stream that passes to the alkylation reaction zone is preferably an aliquot portion of the transalkylation effluent stream. As used herein, the term "aliquot portion of a stream" means a portion of the stream that has essentially the same composition as the stream.

Passing the transalkylation effluent stream to the alkylation zone is itself advantageous. For example, in the production of isopropyl aromatics, this invention decreases the formation of polyisopropyl aromatics, especially diisopropyl aromatics, in the alkylation reaction zone, because polyisopropyl aromatics in the transalkylation effluent that pass to the alkylation zone tend to inhibit the production of polyisopropyl aromatics in the alkylation reaction zone. Because the alkylation reaction zone makes less polyisopropyl aromatics, the transalkylation reaction zone does not need to convert as many polyisopropyl aromatics, and, therefore, the capital and operating costs associated with recycling the alkylation substrate to the transalkylation reaction zone in a combination alkylation-transalkylation process decrease.

The alkylation reaction zone feed stream contains not only components that exit the transalkylation reaction zone but also additional components that are injected into the transalkylation effluent stream. For instance, the alkylating agent (propylene) enters the transalkylation effluent stream between the transalkylation and alkylation reaction zones. In addition, if the quantity of alkylation substrate (benzene) in the transalkylation effluent is insufficient for the alkylation reaction zone or if the temperature in the alkylation reaction zone requires adjustment, then additional fresh or recycle benzene may be combined with the transalkylation effluent stream and passed to the alkylation reaction zone. Of course, as mentioned previously, if additional benzene is required for alkylation, then it may be preferable, subject to transalkylation space velocity constraints, for that benzene to be first passed through the transalkylation reaction zone, where a higher ratio of benzene per diisopropylbenzene and a higher ratio of phenyl groups per propyl groups would tend to increase diisopropylbenzene conversion. Finally, water may be added to the transalkylation effluent stream, because some alkylation catalysts benefit from operating at a higher concentration of water than transalkylation catalysts.

The alkylation reaction zone can operate over a broad range of operating conditions. The alkylation reaction zone is ordinarily operated to obtain an essentially complete conversion of the alkylating agent (propylene) to cumene, diisopropylbenzene, or heavier polyisopropylbenzenes. Propylene conversion is generally more than 99.5% and preferably more than 99.9%. Preferably, the operating conditions result in nearly equilibrium concentrations of cumene being produced in the alkylation reaction zone. The concentration of cumene is generally greater than 80% of the equilibrium concentration, and preferably greater than 95%. To help attain such a high cumene concentration, a stoichiometric excess of benzene over propylene is generally present in the alkylation reaction zone feed. The molar ratio of benzene per propylene is generally from about 20:1 to about 1:1, and preferably from about 5:1 to about 1:1. The preferred molar ratio of phenyl groups per propyl group in the alkylation reaction zone is from about 5:1 to about 1:1. Temperatures usually range from about 210° F. (99° C.) to about the critical temperature of the alkylation substrate, which is about 554° F. (290° C.) for benzene and may be 889° F. (475° C.) or even higher for heavier alkylation substrates. For cumene production temperatures are preferably in the range of about 250 to 350° F. (121 to 177° C.) and more preferably in the range of about 270 to 350° F. (132 to 177° C.), while for ethylbenzene production temperatures are preferably in the range of about 340 to 500° F. (171 to 260° C.). So, preferable temperatures include from about 250 to about 500° F. (121 to 260° C.). Pressures can also vary within a wide range of from about 1 atmosphere to about 130 atmospheres. Because liquid phase conditions are generally preferred within the alkylation reaction zone, the pressure should be sufficient to maintain the benzene in a liquid phase and will typically fall in a range of from 10 to 50 atmospheres. The alkylation reaction zone usually operates under at least partial liquid phase conditions. The benzene liquid hourly space velocity (LHSV) is generally from about 0.5 to about 50 $hr^{-1}$, and preferably from about 1 to about 10 $hr^{-1}$. The water concentration in the alkylation reaction zone is generally greater than 50 wppm, but may be over 500 wppm, depending on the particular catalyst. The propylene concentration in the alkylation reaction zone is generally less than 12 wt-% and preferably less than 6 wt-% in order to minimize formation of alkylation by-products.

Since the alkylation zone in this invention processes only a portion of the flow from the transalkylation effluent, the alkylation zone operates at a decreased space velocity in comparison to alkylation zones in the prior art that process the entire flow from the transalkylation effluent. Advantage can be taken of this reduction in space velocity to reduce the amount of catalyst in the alkylation zone and/or to adjust the flow of alkylating agent to the alkylation zone.

This invention is typically suitable to the case where the stream containing the alkylating agent contains non-alkylating materials, and preferably with low concentrations of the non-alkylating materials. For example, in a cumene process the propylene-containing stream commonly contains some propane. This invention is particularly applicable where the propylene stream of a cumene process contains from 0 to about 50 wt-% propane.

A catalyst promotes the initial alkylation of the alkylation substrate in the alkylation reaction zone. A wide variety of catalysts can be used in the alkylation reaction zone. Suitable catalysts for use in the alkylation reaction zone will comprise any catalyst that is not deactivated rapidly as a consequence of including heavies in the alkylation reaction zone feed. In addition, the presence of heavies should not have a deleterious effect on the approach to equilibrium cumene concentrations in the alkylation reaction zone. If polyisopropylbenzenes are present in the alkylation reaction zone feed, those with fewer propyl groups are preferred, as are low concentrations of any polyisopropylbenzenes that are present. Preferably, the concentration of polyisopropylbenzenes is less than 5 wt-% of the alkylation reaction zone feed. Also, the presence of cumene in the alkylation feed should not have a significant adverse effect on the production of cumene in the alkylation reaction zone.

The preferred alkylation catalyst for use in this invention is a zeolitic catalyst. Suitable zeolites include zeolite Y, zeolite beta, ZSM-5, PSH-3, MCM-22, MCM-36, MCM-49, and MCM-56. Zeolite Y is described in U.S. Pat. No. 3,130,007. A preferred zeolite Y is essentially free of residual non-$H^+$ cations, by which it is meant that the non-$H^+$ cation content of the zeolite Y is less than 200 wppm calculated as $NH_3$ equivalents. Thus, the number of $H^+$ acid sites in the preferred zeolite Y is maximized. Zeolite beta is described in U.S. Pat. No. 3,308,069 and Re 28,341. The topology of zeolite beta and the three zeolite beta polytypes are described in the article by Higgins, et al., in Zeolites, Vol. 8, November 1988, starting at page 446; and in the letter by M. M. J. Treacy et al., in Nature, Vol. 332, Mar. 17, 1988, starting at page 249. Suitable zeolite betas include, but are not limited to, the naturally occurring mixture of the three polytypes, any one of the three polytypes, or any combination of the three polytypes. The use of zeolite beta in alkylation and transalkylation is disclosed in U.S. Pat. Nos. 4,891,458 and 5,081,323, and the use of pristine zeolite beta in alkylation is disclosed in European Patent EP 432,814 B1. Suitable zeolite betas include, but are not limited to, pristine zeolite beta in which the $H^+$ ion has at least partially replaced the contained metal cation, as disclosed in European Patent EP 432,814 B1; and zeolite beta into which certain quantities of alkaline, alkaline-earth, or metallic cations have been introduced by ion exchange, as disclosed in U.S. Pat. No. 5,672,799. Various modifications of zeolite beta are also suitable for use in this invention. Suitable modified zeolite betas include, but are not limited to, zeolite beta which has been modified by steam treatment and ammonium ion treatment, as disclosed in U.S. Pat. No. 5,522,984; and zeolite beta in which the $H^+$ ion has at least partially replaced the contained metal cation, with the zeolite beta being modified by isomorphous substitution of aluminum by boron, gallium, or iron, as disclosed in European Patent EP 432,814 B1. Suitable zeolites for use in this invention also include zeolites that are synthesized by modified preparation methods, such as, but not limited to, a preparation method comprising forming a reaction mixture comprising water, a source of silicon dioxide, a source of fluoride ions, a source of tetraethylammonium cations, and, optionally, a source of an oxide of a trivalent element, as disclosed in PCT International Publication Number WO 97/33830. ZSM-5 is described in U.S. Pat. No. 3,702,886 and Re 29,948. PSH-3 is disclosed in U.S. Pat. No. 4,439,409. MCM-22 is disclosed in U.S. Pat. Nos. 4,954,325 and 4,992,606, and its structure is described in the article in Science, Vol. 264, pp. 1910–1913 (Jun. 24, 1994). U.S. Pat. Nos. 5,077,445; 5,334, 795; and 5,600,048 describe the use of MCM-22 to produce alkylaromatics. MCM-36 is disclosed in U.S. Pat. Nos. 5,250,277 and 5,292,698. The use of a catalyst comprising MCM-36 to produce alkylaromatics such as ethylbenzene is disclosed in U.S. Pat. Nos. 5,258,565 and 5,600,048. The synthesis of MCM-49 is described in U.S. Pat. No. 5,323, 575, and the use of MCM-49 to produce alkylaromatics including the liquid phase production of ethylbenzene is described in U.S. Pat. Nos. 5,371,370; 5,493,065; and 5,600, 048. MCM-56 is disclosed in U.S. Pat. No. 5,362,697. The use of MCM-56 to produce ethylbenzene and other alkylaromatics is disclosed in U.S. Pat. Nos. 5,453,554 and 5,600,048.

A preferred zeolite beta for use in alkylation in this invention is disclosed in U.S. Pat. No. 5,723,710, the teachings of which are incorporated herein by reference. This preferred zeolite is a surface-modified zeolite beta which results from acid washing of a templated native zeolite beta. That is, the formation of the surface-modified zeolite beta starts with a templated beta where the template is, for example, a tetraalkylammonium salt, such as tetraethylammonium salt. It is critical to acid wash a templated zeolite beta in order to protect the internal sites of the zeolite and to prevent dealumination. The templated zeolite beta is treated with a strong acid at a pH between about 0 up to about 2, although a pH under 1 is preferred. Acids which may be used include nitric acid, sulfuric acid, phosphoric acid, and so forth. For example, a weak, 0.01 molar nitric acid may be used in conjunction with ammonium nitrate to perform the acid wash, although substantially higher concentrations, up to about 20 weight percent nitric acid, are preferred. Nitric acid is a preferred acid since it is a non-complexing acid and therefore does not encourage dealumination. Treatment of the templated zeolite beta with strong acid may be effected over the temperature range between about 20° C. (68° F.) up to about 125° C. (257° F.). It is important that acid washing be done under conditions not so severe as to effect dealumination.

The time over which acid washing is conducted in preparing the preferred zeolite is quite temperature dependent. It is critical in the formation of the surface-modified zeolite beta that there be no significant bulk dealumination of the zeolite. Thus, as a general statement it can be said that acid washing should be done for a time insufficient to effect dealumination. For example, using 0.01 molar nitric acid and circa 40% ammonium nitrate at 70° C. (158° F.), contact times of 2–3 hours are found adequate to modify the environment of surface aluminum without causing significant bulk dealumination. Using circa 15% nitric acid with ammonium nitrate to treat a circa 25 weight percent slurry at 85° C. (185° F.), a 90-minute treatment is effective. The dependent variables in acid washing include acid concentration, slurry concentration, time and temperature, and suitable conditions at which surface-modified zeolite beta can be prepared without significant bulk dealumination are readily determined by the skilled artisan.

Next the template is removed by calcination at temperatures in the range of 550–700° C. (1022–1292° F.). Calcination conditions are well known in the art and need not be elaborated upon here. It also needs to be mentioned that powdered zeolite itself is not usually used as the alkylation catalyst. Therefore, in the more usual case after the templated zeolite beta is acid washed it is mixed with a conventional binder, extruded, and the extrudate is ultimately calcined. But the critical portion of the preparation of the preferred zeolite is the acid wash of the templated beta according to the foregoing description. Acid washing a calcined (i.e., non-templated) zeolite beta does not produce the surface-modified material of the preferred zeolite.

It has been found that after treatment as described above the surface aluminum atoms are chemically modified. It has been hypothesized that the modification is in the form of replacement of strong acid sites at the catalyst surface by weaker acid sites. What has been definitely observed is that the surface aluminums of the preferred modified zeolite beta have 2 p binding energies as measured by x-ray photoelectron spectroscopy of at least 74.8 electron volts.

As mentioned previously, the zeolite will usually be used in combination with a refractory inorganic oxide binder. Preferred binders are alumina and silica. Preferred alkylation catalysts include zeolite Y with an alumina or silica binder, and zeolite beta or the previously-described surface-modified zeolite beta with an alumina or silica binder. The zeolite will usually be present in an amount of at least 50 wt-% of the catalyst, and preferably in an amount of at least 70 wt-% of the catalyst.

This process is useful for any arrangement of transalkylation reaction zone and alkylation reaction zone wherein the effluent of the former is passed to the latter. However, it has been found that a beta zeolite or a Y type zeolite contained in an alumina binder will perform very well when used in both the alkylation reaction zone and the transalkylation reaction zone. Therefore, both reaction zones may use the same catalyst. Accordingly, in a preferred embodiment of this invention for cumene production, beta zeolite is used as the catalyst in both the alkylation and transalkylation zones.

There is no requirement, however, that the alkylation reaction zone and the transalkylation reaction zone use the same catalyst. For example, an embodiment for cumene production uses Y zeolite as the transalkylation catalyst and beta zeolite as the alkylation catalyst. This combination of Y zeolite for transalkylation and beta zeolite for alkylation may generally be used for producing cumene when the molar ratio of phenyl groups per isopropyl group in the alkylation zone is less than 3:1, the transalkylation temperature is from about 250 to about 350° F. (121 to 177° C.), and the alkylation temperature is from about 250 to about 350° F. (121 to 177° C.).

There is also no requirement that the transalkylation reaction zone and the alkylation reaction zone be in separate vessels. However, it is believed that an alkylation reaction zone and a transalkylation reaction zone will require less capital expense and be less mechanically complex when both are in a single, common reaction vessel. Therefore, in the preferred embodiment of this invention, both reaction zones are in the same reaction vessel.

The alkylation reaction zone may be operated and arranged in any manner that provides the desired operating temperatures and number of contacting stages. Multiple contacting stages in the alkylation reaction zone are routinely used to provide cooling by the staged addition of reactants and/or cooled reactor effluent quench to multiple beds of alkylation catalyst. The multiple injection of the reactants or quench serves to cool the stages between alkylation catalyst beds, to provide temperature control, and to reduce the concentration of alkylating agent (e.g., propylene).

Ordinarily, the alkylation catalyst is arranged in multiple beds to permit series flow of the alkylation substrate (e.g., benzene) and parallel flow interbed injection of the alkylating agent (e.g., propylene). Thus, in the usual situation, benzene is provided in a molar excess to the olefin, all of the benzene that is provided to the multiple beds is introduced into the first bed, and the effluent of each of the beds flows to the next bed in the series. In this way, unreacted benzene from each bed is made available to react in the next bed in the series. However, where the alkylation catalyst is arranged in multiple beds, the alkylation substrate can also be injected between beds of alkylation catalyst. Multiple beds of alkylation catalyst means two or more beds of alkylation catalyst. In theory, there is no upper limit as to the number of alkylation catalyst beds, but in practice the maximum number of beds of alkylation catalyst is determined by a number of factors, including the ability to distribute flow in each bed uniformly, the ability to inject alkylating agent and/or alkylation substrate to each bed evenly, the exothermic temperature rise in each bed, and the clearance and/or access required to assemble and maintain the mechanical equipment associated with each bed. A typical alkylation unit usually has 4 or 6 alkylation catalyst beds, but it is also possible to have as many as 10, 20, or more alkylation catalyst beds.

The portion of the transalkylation effluent stream that passes to a multibed alkylation reaction zone may itself be divided into sub-portions, preferably aliquot sub-portions. As used herein, the term "aliquot sub-portion of a portion" means a sub-portion of the portion that has essentially the same composition as the portion. One sub-portion of the transalkylation effluent stream may pass to the first bed in the series, and a second sub-portion may pass to another bed in the series. In the case where there are only two alkylation catalyst beds, between about 0 and about 99% of the portion of the transalkylation effluent stream that passes to the alkylation reaction zone passes to the first bed in the series, and the remainder, i.e., between about 1 and about 100% of the transalkylation effluent stream that passes to the alkylation reaction zone, passes to the second alkylation bed. Where there are three or more alkylation catalyst beds, between about 0 and about 99% of the portion of the transalkylation effluent stream that passes to the alkylation reaction zone passes to the first bed in the series, and for any other alkylation bed in the series, between about 0 and about 100% of the portion of the transalkylation effluent stream that passes to the alkylation reaction zone passes to that other bed in the series. Thus, where a portion of the transalkylation effluent passes stage-wise to an alkylation reaction zone having four alkylation catalyst beds, numerous possibilities for the distribution of the portions of the transalkylation effluent exist. One possibility is 25% to each of the four beds. A second possible distribution is 10% to the first bed, 40% to the second bed, 0% to the third bed, and 50% to the fourth bed. A third possible distribution is 30% to the first bed, 10% to the second bed, 60% to the third bed, and 0% to the fourth bed. Because the transalkylation effluent is generally at a temperature that is less than the effluent temperature of each alkylation bed, the transalkylation effluent that is injected between the alkylation beds can provide not only multiple injection of reactants but also quench for the alkylation catalyst beds.

Where alkylation substrate is injected directly to one or more beds of alkylation catalyst, there are numerous possible distributions for the portions of the alkylation substrate. In the case of only two alkylation catalyst beds, between about 0 and about 100% of the alkylation substrate that passes directly to the alkylation reaction zone passes to the first bed in the series, and the remainder, i.e., between about 0 and about 100% of the alkylation substrate that passes to the alkylation reaction zone, passes to the second alkylation bed. In the case of three or more alkylation catalyst beds, between about 0 and about 100% of the portion of the alkylation substrate that passes to the alkylation reaction zone passes to the first bed in the series, and for any other alkylation bed in the series, between about 0 and about 100% of the portion of the alkylation substrate that passes to the alkylation reaction zone passes to that other bed in the series. Where there are four alkylation catalyst beds in the alkylation reaction zone, some of the possible distributions of the portions of the alkylation substrate are: 25% to each of the four beds; 0% to the first bed, 20% to the second bed, 30% to the third bed, and 50% to the fourth bed; 50% to the first bed, 50% to the second bed, 0% to the third bed, and 0% to the fourth bed; 100% to the first bed, and 0% to each of the second, third, and fourth beds.

Many combinations of transalkylation effluent distributions and alkylation substrate distributions to the alkylation beds are possible, and the description of possible combinations that are described herein is not intended to limit the scope of the invention as set forth in the claims. For example, for a given number of alkylation catalyst beds, any of the individual distributions of the portion of the transalkylation effluent described herein may be combined with any of the individual distributions of alkylation substrate described herein. One example comprises directing to each alkylation bed essentially equal portions of the portion of the transalkylation effluent that passes to the alkylation reaction zone while directing to each alkylation bed essentially equal portions of the alkylation substrate that passes directly to the alkylation reaction zone. However, particular combinations of the portion of the transalkylation effluent and alkylation substrate distributions are believed to decrease the formation of heavies by-products such as diphenylpropane and alkylated diphenylpropanes. Particularly desirable combinations of transalkylation effluent distributions and alkylation substrate distributions to a series of alkylation beds include those in which the first bed receives from about 0 to about 50% of the portion of the transalkylation effluent that passes to the alkylation reaction zone, and about 50 to about 100% of the alkylation substrate that passes directly to the alkylation reaction zone. Other desirable combinations of distributions are those in which, compared to the bed that is immediately upstream, each bed in the series receives a larger portion of the portion of the transalkylation effluent that passes to the alkylation reaction zone and a smaller portion of the alkylation substrate that passes directly to the alkylation reaction zone.

Where the alkylation reaction zone contains separate alkylation catalyst beds, the separate beds may be arranged in a single vessel or in multiple vessels. In practicing this invention with multiple alkylation catalyst beds, a common vessel may contain the transalkylation reaction zone and one or more alkylation reaction catalyst beds. However, for very large units separate vessels for the transalkylation catalyst bed and for one or more alkylation catalyst beds may be more advantageous.

The alkylation effluent generally is a mixture of the desired monoalkyl aromatic product with a wide variety of undesired by-products. For example, in the alkylation of benzene with propylene to produce cumene, the reaction zone can produce diisopropylbenzenes, triisopropylbenzenes, tetraisopropylbenzenes, heavier polyisopropylbenzenes, and other heavies such as diphenylpropane in addition to other propylene condensation by-products. Transalkylation also yields additional alkyl aromatic by-products, which in this invention can be alkylated in the alkylation reaction zone to produce still other by-products. Generally, the alkylation effluent stream also contains a substantial amount of unreacted aromatic substrate (benzene), because aromatic substrate is ordinarily present in a stoichiometric excess in both transalkylation and alkylation. Therefore, a number of separation stages are needed to separate the desired aromatic product from the by-products and the unreacted aromatic substrate.

As mentioned previously, passing some of the transalkylation effluent stream to the product recovery zone is an essential element of this invention. In effect, the portion of the transalkylation effluent stream that passes directly to the product recovery zone bypasses the alkylation reaction zone. This portion is generally from about 0.5 to about 99.5% of the transalkylation effluent stream, commonly from about 5 to about 75%, and more commonly from about 10 to about 50%. The portion of the transalkylation effluent stream that passes to the product recovery zone is preferably an aliquot portion of the transalkylation effluent stream.

A number of combinations of columns and separators can be used to recover the desired isopropyl aromatic product and to produce recycle streams of aromatic substrate and polyisopropyl aromatics for transalkylation. Typically, a first column separates light paraffins that entered the process with the alkylating agent and that passed through the alkylation reaction zone without reacting. A second column separates the aromatic substrate from the remaining heavier components of the alkylation effluent stream. Alternatively, the order of these first two columns may be reversed, in which case a low alkane (e.g., propane) content of the alkylating agent stream (e.g., propylene-containing stream) is preferred. One or more additional separation columns separate the desired aromatic product from by-product streams that contain lighter or heavier by-products. Some heavies by-products, such as dialkyl, trialkyl, and even tetralkyl aromatics, may under some circumstances be recycled to transalkylation. But heavies by-products that are not suitable or are not desirable for transalkylation are usually rejected from the process.

In one embodiment of this invention, the effluent of any alkylation catalyst bed is divided into at least two aliquot portions. In this embodiment, one aliquot portion of an alkylation catalyst bed effluent passes to another alkylation catalyst bed in the series of alkylation beds that is downstream in relation to the alkylation catalyst bed from which the effluent is withdrawn, except if this aliquot portion is withdrawn from the last alkylation catalyst bed in the series, in which case this aliquot portion passes to the aforementioned columns and separators to recover the desired isopropyl aromatic product and to produce recycle streams. In addition, in this embodiment at least one other aliquot portion of the alkylation catalyst bed effluent is recycled either to the alkylation catalyst bed from which the effluent is withdrawn or to another alkylation catalyst bed in the series of alkylation beds that is upstream in relation to the alkylation catalyst bed from which the effluent is withdrawn. An aliquot portion that is introduced into an alkylation catalyst bed may be cooled and is preferably introduced into the inlet of the alkylation catalyst bed. In this embodiment, an aliquot portion of the transalkylation effluent may pass to one of the beds, or a plurality of aliquot portions of transalkylation effluent may pass to a plurality of beds, including beds to which alkylation effluent is introduced. For a bed into which an alkylation effluent portion is recycled and to which transalkylation effluent is also passed, the flow rate of the alkylation effluent portion relative to that of the transalkylation effluent portion is selected depending on several factors, including the inlet temperature and the maximum temperature in the bed, which can in turn influence the deactivation rate of the catalyst, the production of desired product, and the production of byproducts in the bed. For the production of cumene, the inlet temperature of such a bed is usually from about 250 to about 280° F. (121 to 138° C.), but may be higher or lower than this range. The maximum temperature of such a bed is usually from about 290 to about 350° F. (143 to 177° C.), and may be higher or lower than this range.

An example of recycling alkylation effluent in an embodiment of the present invention having an alkylation reaction zone comprising a single alkylation reactor containing two alkylation catalyst beds in series is passing one aliquot portion of the effluent from the second alkylation bed to the columns and separators for product recovery while recycling one or more other portions to the first alkylation bed, the second alkylation bed, or both. In another example, wherein an alkylation reaction zone has two alkylation reactors in a series flow arrangement and wherein each reactor contains two catalyst beds in a series flow arrangement, an aliquot portion of the effluent of the downstream bed of the downstream reactor may be recycled to the upstream bed of the upstream reactor, to the upstream bed of the downstream reactor, or to both upstream beds. Similarly, an aliquot portion of the transalkylation effluent may pass to the upstream bed of the upstream reactor, to the upstream bed of the downstream reactor, or to both upstream beds.

The operation of this invention and of an arrangement of separation zones to recover product and to produce recycle streams can be better understood by referring to FIG. 1. FIG. 1 schematically illustrates the major equipment used in performing the process of this invention for the production of cumene. In the process, fresh benzene feed flows through line 76 and mixes with a stream in line 102 that contains recycle benzene, as well as recycle diisopropylbenzenes and triisopropylbenzenes. The mixture flows through line 104 and enters a bed 12 of zeolitic transalkylation catalyst. A vessel 10 houses the transalkylation bed 12. After contact with the catalyst in bed 12, the transalkylation zone effluent from bed 12 exits from vessel 10 via line 14, and splits into two portions. One portion of the transalkylation zone effluent flows through line 16 to the junction of lines 54 and 56, and thereby bypasses the alkylation beds 32, 34, 53, and 55. The other portion of the transalkylation effluent flows through line 18, and passes through an indirect heat exchanger 20, which, if necessary, heats or cools the transalkylation effluent portion in line 18 to a suitable temperature prior to passing to vessel 30. This portion of the transalkylation effluent then passes through line 22, receives propylene via line 24, and flows through line 26. The mixture of transalkylation effluent and propylene in line 26 combines with a stream in line 66 that contains a mixture of recycle alkylation effluent and recycle benzene, and the combined stream enters by line 28 into bed 32 of zeolitic alkylation catalyst. Vessel 30 houses alkylation bed 32 and an additional alkylation bed 34. Effluent from bed 32 receives propylene via line 36, and enters bed 34 which contains zeolitic alkylation catalyst. Alkylation bed 34 effluent flows from vessel 30 via line 38 and passes through indirect heat exchanger 40 which removes the exothermic heat of the alkylation reaction and cools the alkylation bed effluent to a suitable temperature prior to passing to vessel 50. The cooled alkylation effluent flows through line 42, receives propylene via line 44, and passes through line 46 to vessel 50, which contains another pair of alkylation beds 53 and 55, each of contains zeolitic alkylation catalyst. The stream in line 46 enters bed 53, and bed 53 effluent combines with propylene in line 48 and enters bed 55. Incidentally, water (not shown) may be injected into any, some, or all of the alkylation beds. Alkylation zone effluent from alkylation bed 55 flows from vessel 50 via a line 52.

The alkylation zone effluent in line 52 from vessel 50 splits into two portions. One portion flows through line 58, is cooled in indirect heat exchanger 60 which removes the exothermic heat of reaction, passes through line 62, and mixes with recycle benzene flowing in line 64. The mixture of alkylation zone effluent and benzene flows through line 66, and, as described previously, combines with the stream in line 26 and enters via line 28 into alkylation bed 32. Although not shown in FIG. 1, line 62 may optionally supply alkylation zone effluent directly to each or any of the other alkylation beds 34, 53, or 55 by recycling to a point upstream of each or any such bed. Likewise, line 64 may optionally supply benzene directly to each or any of the other alkylation beds 34, 53, or 55 by recycling to a point upstream of each or any such bed. The other portion of the alkylation zone effluent flows through line 54 and combines with the portion of the transalkylation zone effluent that bypassed the alkylation beds by flowing through line 16. The combined portions of alkylation zone effluent and transalkylation zone effluent flow through line 56 and enter benzene column 70. From benzene column 70 are withdrawn a fraction containing benzene and light hydrocarbons in line 72 and a bottom stream containing higher boiling hydrocarbons in line 68. The fraction, which typically contains propane that entered the process via lines 24, 36, 44, and 48 with the propylene feed, passes through line 72 to a depropanizer 80. Although not shown in the FIG. 1, a portion of the fraction in line 72 may optionally be recycled to a point upstream of alkylation bed 32 in vessel 30 to provide additional benzene with a relatively high water concentration for the alkylation reaction zone.

Depropanizer 80 produces an overhead stream containing propane and water that is recovered in line 74. A purified benzene stream having a relatively low water concentration is also recovered from depropanizer 80 via line 82 for recycle. This recycle benzene in line 82 divides into two portions. One portion flows through line 64 and combines with the recycled portion of the alkylation effluent stream in line 62, which, as described previously, forms a combined stream that passes through lines 66 and 28 to vessel 30. Another portion of the recycle benzene flows through line 86 and combines with recycle diisopropylbenzenes and triisopropylbenzenes flowing in line 98 to form the previously-described stream in line 102.

Line 68 carries the bottom stream of the benzene column 70 to a cumene column 90. Line 88 recovers a cumene product overhead, and line 92 transfers a bottoms stream to a heavies column 100 for the recovery of diisopropylbenzene and triisopropylbenzene via a line 98, a lighter boiling material via line 96, and heavies via line 94. A purified stream of diisopropylbenzene and triisopropylbenzene in line 98 is recycled to transalkylation bed 12 via lines 102 and 104, as described previously. Alternatively, some or all of the triisopropylbenzene in line 92 can be removed from column 100 with the heavies via line 94.

Passing all of the recycle benzene that flows through the line 82 to transalkylation reactor 12 via line 86 is advantageous in comparison with diverting a portion of the recycle benzene in line 82 around the transalkylation bed 12 and then passing that portion directly to the first alkylation bed 32. This advantage arises because any phenyl groups passed to transalkylation bed 12 ultimately pass to the alkylation beds 32, 34, 53 and 55. Therefore, passing all of the recycle benzene to the transalkylation reactor increases the phenyl/ethyl ratio in the transalkylation reactor without decreasing the phenyl/ethyl ratio in the alkylation beds.

Passing the fresh benzene feed that flows through line 76 to benzene column 70 via introduction to line 56, or to depropanizer 80 via introduction to line 72, may be advantageous. In comparison with passing the fresh benzene feed to the junction of lines 102 and 104 as shown in FIG. 1, the former case is advantageous because benzene column 70 can remove via line 68 components in the fresh benzene feed that are heavier than benzene, and either case is advantageous because depropanizer 80 can remove via line 74 components in the fresh benzene feed that are lighter than benzene. In either case, the flow of benzene through the line 82 to transalkylation reactor 12 via line 86 is preferably at least equal to the flow of benzene flowing through line 76.

The following examples illustrate embodiments of this invention and are not intended to limit the scope of this invention as set forth in the claims. These examples are based on engineering calculations, yield predictions, and experience with similar processes.

EXAMPLES

In Examples A–F, and for the purposes of illustrating the present invention, it is presumed that it is impractical to operate the alkylation zone at a benzene/olefin ratio below 1:1. This is a reasonable presumption, since it is believed that the most widely practiced application of the present invention is to the monoalkylation of the aromatic substrate with the alkylating agent to produce the desired alkyl aromatic product (e.g., monoalkylation of benzene with ethylene to produce ethylbenzene, or with propylene to produce cumene). When the desired alkyl aromatic product has only one more alkyl group than the aromatic substrate, alkylating with a benzenelolefin ratio of less than 1:1, while feasible, will often produce excessive amounts of polyalkyl aromatics in alkylation. However, in making this presumption, it is not intended to limit the present invention to processes in which the alkylation zone operates at a benzene/olefin ratio of not less 1:1. Nor is it intended for this presumption to limit the scope of the invention as set forth in the claims.

In Examples A–F, it is also presumed that it is possible to operate the alkylation zone at a benzene/olefin ratio as low as 1:1. Whether the alkylation zone can operate as low as 1:1 benzene/olefin ratio depends on several factors, including the performance of the alkylation catalyst with respect to its stability (e.g., catalyst life), yield of the desired alkyl aromatic product, and selectivity to the desired product; mechanical constraints or other limitations of the equipment in the alkylation zone; performance of the transalkylation catalyst; and transalkylation operating conditions. However, for several reasons, it is believed that commercial alkylation catalysts can suitably operate as low as 1:1 benzene/olefin ratio. First, alkylation catalysts, including the preferred alkylation catalyst previously described herein, are increasingly robust and selective, even at low benzene/olefin ratios. Second, it is common for commercial alkylation zones to be designed mechanically to use solid alkylation catalyst and to operate at low benzene/olefin ratios. Finally, suitable commercial transalkylation catalysts are available and suitable transalkylation conditions can be selected so that, even if operation at low benzene/olefin ratios in alkylation results in unacceptably high yields of polyalkyl aromatics in alkylation, the transalkylation zone can be operated at a sufficiently high conversion so as to convert the polyalkyl aromatics to monoalkyl aromatics. Therefore, it is within the skill of a person of ordinary skill in the art to operate the alkylation zone at a benzene/olefin ratio as low as 1:1.

Figure 2:
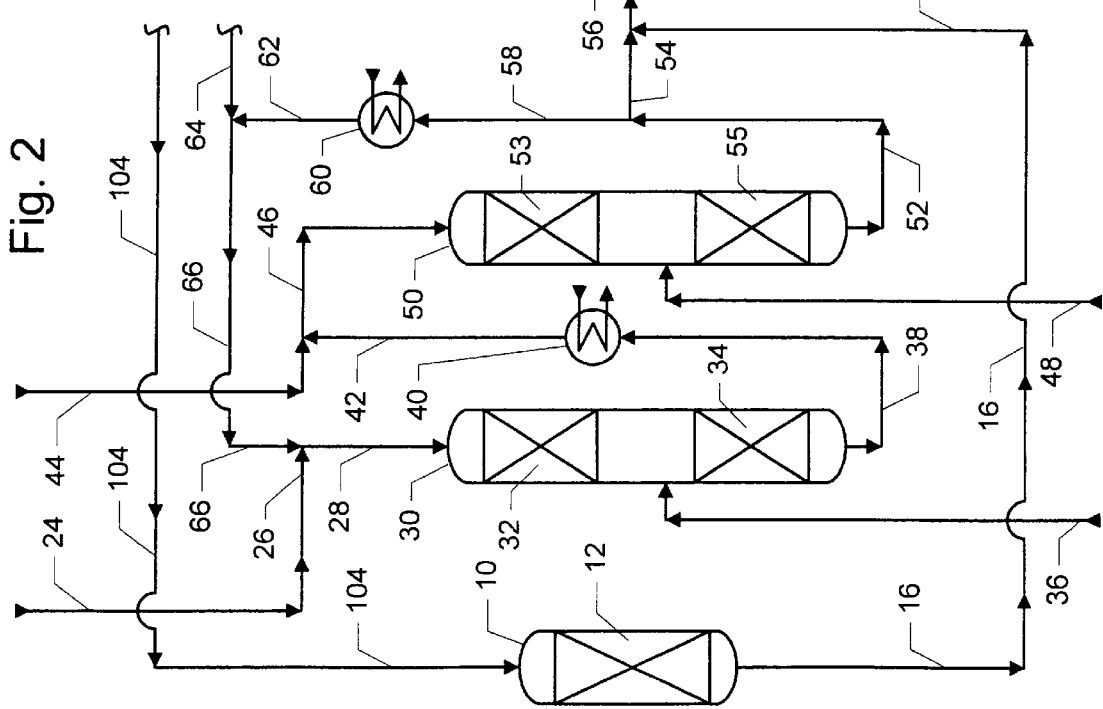

FIG. 2 illustrates a prior art combination process, which does not use the present invention. The flow scheme for FIG. 2 is a variation of that in FIG. 1. For the sake of brevity, lines and equipment of the product recovery zone that are shown in FIG. 1 are not again shown in FIG. 2, and lines in FIG. 2 which interconnect with lines in FIG. 1 have the same line numbers in both FIGS. 1 and 2. FIG. 2 omits lines 18 and 22 and exchanger 20, which are shown in FIG. 1. Thus, in FIG. 2 the transalkylation effluent stream in line 16 does not split into two portions but instead flows in its entirety to line 56. Accordingly, in FIG. 2 no transalkylation effluent passes to vessel 30, which is instead fed with a combined stream in line 28 formed from the propylene-containing stream in line 24, the recycle benzene stream in line 64, and the recycle alkylation effluent stream in line 62. Therefore, the flows through transalkylation and alkylation in FIG. 2 can thus be considered as being in parallel.

Figure 3:
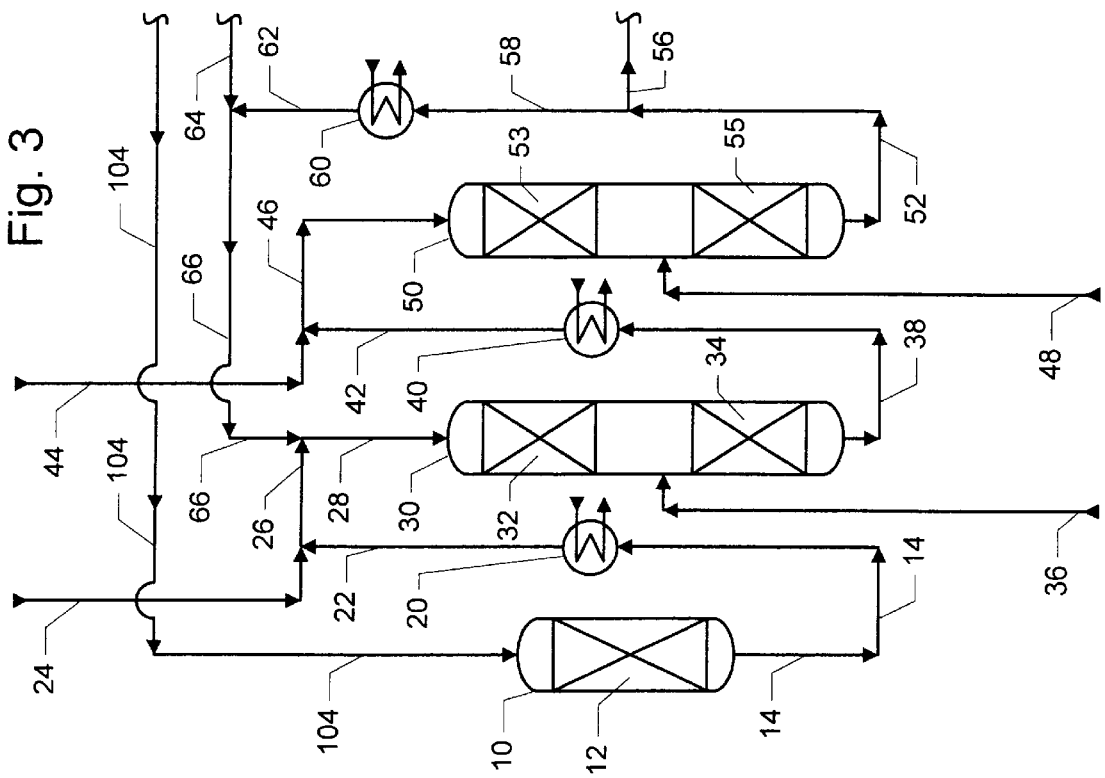
FIGS. 2 and 3 are schematic illustrations of prior art processes.

FIG. 3 illustrates another prior art combination process, which also does not use the present invention. The flow scheme for FIG. 3 is another variation of that in FIG. 1. For the sake of brevity, lines and equipment of the product recovery zone that are shown in FIG. 1 are not again shown in FIG. 3, and lines in FIG. 3 which interconnect with lines in FIG. 1 have the same line numbers in both FIGS. 1 and 3. FIG. 3 omits line 16, which is shown in FIG. 1. Thus, in FIG. 3 the transalkylation effluent stream in line 14 does not split into two portions but instead flows in its entirety through line 14, exchanger 20, and line 22 to the junction of lines 24 and 26. Accordingly, in FIG. 3 all of the transalkylation effluent passes to vessel 30, which is thus fed with a combined stream in line 28 formed not only from the propylene-containing stream in line 24, the recycle benzene stream in line 64, and the recycle alkylation effluent stream in line 62, but also from the transalkylation effluent stream in line 22. Therefore, the flow through transalkylation and alkylation in FIG. 3 can thus be considered as being in series, or "cascaded."

Figure 4:
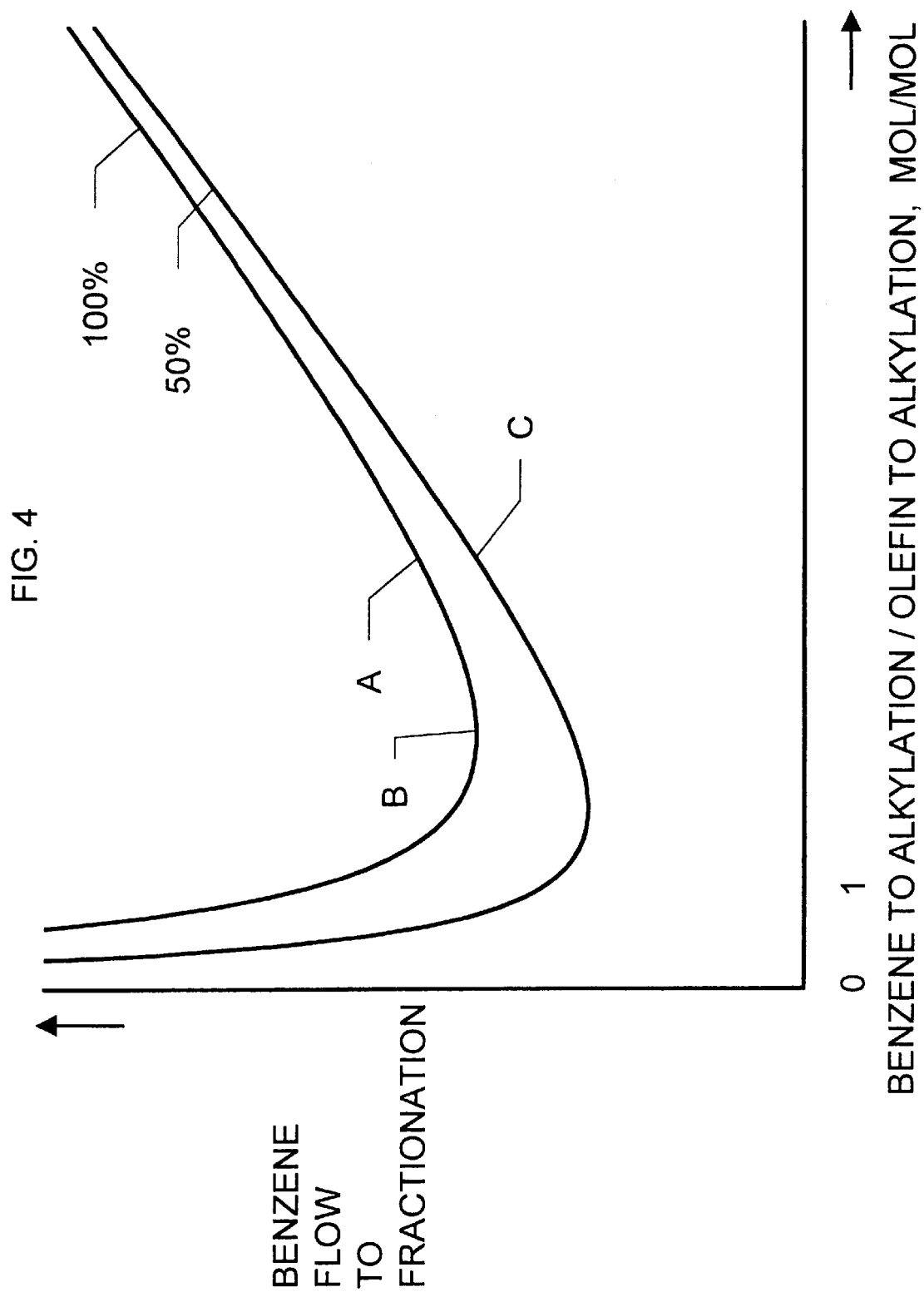

FIG. 4 is an x-y chart, in which the y-axis is the relative flow rate of benzene in line 56 to benzene column 70, and the x-axis is the overall molar ratio of benzene per olefin in alkylation. The numerator of this benzene:olefin ratio is the total moles of benzene flowing in line 28 to the alkylation beds. The denominator is the total moles of propylene passed to the alkylation beds, which is computed by summing the moles of propylene entering through lines 24, 36, 44, and 48. Each of the two curves in FIG. 4 corresponds to a ratio of the flow rate of the portion of the transalkylation effluent that passes through line 16 and via line 56 directly to benzene column 70 divided by the total flow rate of transalkylation effluent exiting from vessel 10, multiplied by 100. Therefore, each curve corresponds to the percentage of the transalkylation effluent stream that bypasses the alkylation reaction zone and flows directly to the product recovery section. Accordingly, the "100%" curve corresponds to all, or 100%, of the transalkylation effluent bypassing the alkylation reaction zone, and thus corresponds to the prior art flow scheme in FIG. 2. The "50%" curve corresponds to half of the transalkylation effluent flowing to the alkylation reaction zone and half of the transalkylation effluent bypassing the alkylation reaction zone. Thus, the "50%" curve corresponds to an embodiment of this invention that can be practiced by the innovative flow scheme in FIG. 1, in which 50% of the transalkylation effluent in line 14 flows to vessel 30 via line 18, exchanger 20, and lines 22, 26, and 28, and 50% of the transalkylation effluent in line 14 flows to benzene column 70 via lines 16 and 56.

FIG. 5 is another x-y chart that has the same axes and the same "100%" curve as FIG. 4, and also has a "0%" curve and a "10%" curve. The "0%" curve corresponds to none, or 0%, of the transalkylation effluent bypassing the alkylation reaction zone, and thus corresponds to the prior art flow scheme in FIG. 3. The "10%" curve corresponds to 90% of the transalkylation effluent flowing to the alkylation reaction zone and 10% of the transalkylation effluent bypassing the alkylation reaction zone. Thus, the "10%" curve corresponds to an embodiment of this invention that also can be practiced by the innovative flow scheme in FIG. 1, in which 90% of the transalkylation effluent in line 14 flows to vessel 30 via line 18, exchanger 20, and lines 22, 26, and 28, and 10% of the transalkylation effluent in line 14 flows to benzene column 70 via lines 16 and 56.

The exact shapes of the curves in FIGS. 4 and 5 depend on the operating conditions for the alkylation and transalkylation zones. However, the curves are computed based on operating conditions that are representative of commercial operating conditions. Each curve is concave upward, and thus for a given amount of bypassing of transalkylation effluent around alkylation, the benzene flow rate to fractionation is at a minimum at a certain, intermediate, and optimum benzene/olefin molar ratio in alkylation. In addition, as the amount of bypassing of transalkylation effluent around alkylation decreases the minimum benzene flow rate to fractionation decreases, and the optimum benzene/olefin ratio decreases.

Examples A, B, and C refer to FIGS. 1, 2, and 4.

Comparative Example A

Example A does not use the present invention. The flow scheme for Example A is shown in FIG. 2. The benzene flow rate to the product recovery section is the rate corresponding to the point in FIG. 4 on the "100%" curve labeled "A."

Comparative Example B

Example B does not use the present invention. The flow scheme for Example B is shown in FIG. 2. The benzene flow rate to the product recovery section is the rate corresponding to the point in FIG. 4 on the "100%" curve labeled B. This benzene flow rate is the minimum flow rate for 100% bypassing of transalkylation effluent. Compared to Example A, the benzene flow rate for Example B is indeed less, but this lower flow rate corresponds to operation at a lower overall benzene/olefin ratio in alkylation, and thus to a higher production of polypropyl benzenes in alkylation. Thus, compared to Example A, Example B has the disadvantage of requiring greater transalkylation capability, such as a larger transalkylation reactor.

Example C

Example C uses the present invention and results in a benzene flow rate to the product recovery section that is the same as that for Example B at an overall benzene/olefin ratio that is the same as that for Example A. The flow scheme for Example C is that shown in FIG. 1, where 50% of the transalkylation effluent passes to alkylation and 50% bypasses the alkylation reaction zone and passes directly to the product recovery section. The benzene/olefin molar ratio is the same as that for Example A, and the benzene flow rate to the product recovery section is the rate corresponding to the point in FIG. 4 on the "50%" curve labeled "C," which is a benzene flow rate that is lower than that for Example A and the same as that for Example B. Thus, unlike Examples A and B, Example C has the advantages of both a low benzene flow rate and a high benzene/olefin ratio.

Examples D, E, and F refer to FIGS. 1, 3, and 5.

Comparative Example D

Example D does not use the present invention. The flow scheme for Example D is that shown in FIG. 2. The benzene flow rate to the product recovery section is the rate corresponding to the point in FIG. 5 on the "100%" curve labeled "D." This benzene flow is the minimum flow rate for 100% bypassing of transalkylation effluent.

Comparative Example E

Example E does not use the present invention. The flow scheme for Example E is shown in FIG. 3. The benzene flow rate to the product recovery section is the rate corresponding to the point in FIG. 5 on the "0%" curve labeled E. This benzene flow rate is the minimum flow rate for 0% bypassing of transalkylation effluent. Compared to Example D, the benzene flow rate for Example E is less, but this lower flow rate corresponds to an undesirable operation at an overall benzene/olefin ratio in alkylation which is less than 1:1. Operation at an overall benzene/olefin ratio in alkylation of less than 1:1 is undesirable when the desired reaction is mono-alkylation of benzene with olefin, since this usually results in excessive production of dialkyl and higher alkyl benzenes. Thus, Example E has the disadvantage of low selectivity to monoalkyl benzenes.

Example F

Example F uses the present invention and results in a benzene flow rate to the product recovery section that is minimized for 10% bypassing of transalkylation effluent at an overall benzene/olefin ratio in alkylation of 1:1. The flow scheme for Example F is that shown in FIG. 1, where 90% of the transalkylation effluent passes to alkylation and 10% bypasses the alkylation reaction zone and passes directly to the product recovery section. The benzene/olefin molar ratio in alkylation is 1:1, and the benzene flow rate to the product recovery section is the rate corresponding to the point in FIG. 5 on the "10%" curve labeled "F," which is the minimum benzene flow rate for 10% bypassing of transalkylation effluent. Thus, Example F has the advantage of operating at the minimum benzene flow rate on its curve. But unlike Example E, Example F operates at this lowest possible benzene flow rate while still maintaining an overall benzene/olefin ratio in alkylation of 1:1.

Therefore, Example F's 10% bypassing of transalkylation effluent is optimally efficient in the sense that it permits operation at the minimum benzene flow rate at the minimum benzene/olefin ratio for producing monoalkyl benzene. Example D's 100% bypassing is not optimally efficient, because the minimum benzene flow rate of the "100%" curve is not only higher than that for Example F but also occurs at a benzene/olefin ratio that is higher than the minimum benzene/olefin ratio for producing monoalkyl benzene. Example E's 0% bypassing is also not optimally efficient because the minimum benzene flow rate occurs at a benzenelolefin ratio that is lower than the minimum benzene/olefin ratio for producing monoalkyl benzene.

Comparative Example G

Example G illustrates the lack of operating flexibility that a prior art process causes in the event that an operational upset occurs in the transalkylation zone.

The process of FIG. 3 is operating at a given quantity of polyalkyl aromatics being converted to monoalkyl aromatics per unit time across transalkylation bed 12. An unexpected temporary ingress of an excessive amount of water enters into vessel 10, such as via a slug of water in the fresh benzene feed flowing through line 76. The quantity of polyalkyl aromatics being converted to monoalkyl aromatics per unit time across transalkylation bed 12 decreases. To increase the polyalkyl aromatics being converted to monoalkyl aromatics per unit time to the quantity per unit time prior to the upset, the flow rate of polyalkyl aromatics passing to transalkylation bed 12 must be increased. The benzene flow rate to transalkylation bed 12 must also be increased, in proportion to the increased flow rate of polyalkyl aromatics, in order to maintain a constant molar ratio of phenyl groups to alkyl groups in transalkylation bed 12. As a result of the increases in these two flow rates to transalkylation bed 12, a corresponding increase in the flow rate entering alkylation bed 32 occurs, since none of the transalkylation effluent flowing in line 14 bypasses the alkylation beds. At a given set of operating conditions in alkylation beds 32, 34, 53, and 55, however, this increased flow rate to the alkylation beds increases the production of aromatics heavier than trialkyl aromatics, which are rejected from the process via line 94. This, in turn, causes a loss in monoalkyl aromatic yield. Thus, this Example G shows that, in the prior art processes, until the quantity of polyalkyl aromatics being converted to monoalkyl aromatics per unit time in transalkylation bed 12 is restored to that prior to an upset in the transalkylation bed 12, the upset propagates to the alkylation beds and results in lost monoalkyl aromatic yield.

Example H

Example H illustrates the extra degree of operating flexibility that this invention allows in the event that an operational upset occurs in the transalkylation zone.

The process of FIG. 1 is operating at a given quantity of polyalkyl aromatics being converted to monoalkyl aromatics per unit time across transalkylation bed 12. An unexpected temporary ingress of an excessive amount of water enters into vessel 10, such as via a slug of water in the fresh benzene feed flowing through line 76. The quantity of polyalkyl aromatics being converted to monoalkyl aromatics per unit time across transalkylation bed 12 decreases. To increase the polyalkyl aromatics being converted to monoalkyl aromatics per unit time to the quantity per unit time prior to the upset, the flow rate of polyalkyl aromatics passing to transalkylation bed 12 must be increased. The benzene flow rate to transalkylation bed 12 must also be increased, in proportion to the increased flow rate of polyalkyl aromatics, in order to maintain a constant molar ratio of phenyl groups to alkyl groups in transalkylation bed 12. Despite the increases in these two flow rates to transalkylation bed 12, a corresponding increase in the flow rate entering alkylation bed 32 does not occur, since a portion of the transalkylation effluent flowing in line 14 bypasses the alkylation beds. Therefore, any increase in transalkylation effluent flow is sent to fractionation via line 16. This, in turn, allows operation of the alkylation beds at the given set of operating conditions and the given entering flow rate from transalkylation that existed prior to the upset. Consequently, there is no loss in monoalkyl aromatic yield. Thus, this Example H shows that, in the process of this invention, even while the quantity of polyalkyl aromatics being converted to monoalkyl aromatics per unit time in transalkylation bed 12 has yet been restored to that prior to an upset in the transalkylation bed 12, the upset does not propagate to the alkylation beds and does not result in lost monoalkyl aromatic yield.

What is claimed is:

1. A process for producing alkyl aromatic hydrocarbons, said process comprising:
   a) passing a first transalkylation feed stream comprising an aromatic substrate hydrocarbon to a transalkylation reaction zone, passing a second transalkylation feed stream comprising a first alkyl aromatic hydrocarbon having more than one alkyl group to said transalkylation reaction zone, transalkylating said aromatic substrate hydrocarbon with said first alkyl aromatic hydrocarbon in the presence of a first solid catalyst in said transalkylation reaction zone to produce a second alkyl aromatic hydrocarbon having at least one more alkyl group than said aromatic substrate hydrocarbon, and recovering from said transalkylation reaction zone a transalkylation effluent stream comprising said aromatic substrate hydrocarbon and said second alkyl aromatic hydrocarbon;
   b) passing a first alkylation feed stream comprising an alkylating agent to an alkylation reaction zone, passing a first aliquot portion of said transalkylation effluent stream to said alkylation reaction zone, and alkylating said aromatic substrate hydrocarbon with said alkylating agent in the presence of a second solid catalyst in said alkylation zone to produce an alkylation effluent stream comprising said second alkyl aromatic hydrocarbon;
   c) passing at least a portion of said alkylation effluent stream and a second aliquot portion of said transalkylation effluent stream to a product separation zone, separating compounds passed to the product separation zone into a product stream comprising said second alkyl aromatic hydrocarbon, a first recycle stream comprising said aromatic substrate, and a second recycle stream comprising said first alkyl aromatic hydrocarbon;
   d) forming at least a portion of said first transalkylation feed stream from at least a portion of said first recycle stream; and
   e) forming at least a portion of said second transalkylation feed stream from at least a portion of said second recycle stream.

2. The process of claim 1 wherein said at least a portion of said alkylation effluent stream comprises an aliquot portion of said alkylation effluent stream.

3. The process of claim 1 further characterized in that said first aliquot portion of said transalkylation effluent stream comprises from about 0.5 to about 99.5% of said transalkylation effluent stream.

4. The process of claim 1 further characterized in that said second aliquot portion of said transalkylation effluent stream comprises from about 0.5 to about 99.5% of said transalkylation effluent stream.

5. The process of claim 1 further characterized in that a second alkylation feed stream comprising said aromatic substrate hydrocarbon is passed to said alkylation reaction zone.

6. The process of claim 1 further characterized in that said alkylation reaction zone contains a plurality of beds containing solid catalyst, at least one bed of said plurality of beds contains said second solid catalyst, and said aromatic substrate hydrocarbon is alkylated with said alkylating agent in said plurality of beds.

7. The process of claim 6 further characterized in that said plurality of beds comprises a first bed and a second bed, and said passing said first alkylation feed stream to said alkylation reaction zone comprises passing a first bed feed stream comprising said alkylating agent to said first bed and passing a second bed feed stream comprising said alkylating agent to said second bed.

8. The process of claim 6 further characterized in that said plurality of beds comprises a first bed and a second bed, and said passing a first aliquot portion of said transalkylation effluent stream to said alkylation reaction zone comprises passing a first aliquot sub-portion of said first aliquot portion to said first bed and passing a second aliquot sub-portion of said first aliquot portion to said second bed.

9. The process of claim 6 further characterized in that said plurality of beds comprises a first bed and a second bed, a first bed feed stream comprising said aromatic substrate hydrocarbon passes to said first bed, and a second bed feed stream comprising said aromatic substrate hydrocarbon passes to said second bed.

10. The process of claim 1 wherein said first solid catalyst comprises a zeolite selected from the group consisting of zeolite Y, zeolite beta, ZSM-5, PSH-3, MCM-22, MCM-36, MCM-49, and MCM-56.

11. The process of claim 1 wherein said second solid catalyst comprises a zeolite selected from the group consisting of zeolite Y, zeolite beta, ZSM-5, PSH-3, MCM-22, MCM-36, MCM-49, and MCM-56.

12. The process of claim 1 wherein said first solid catalyst comprises zeolite Y and said second solid catalyst comprises zeolite beta.

13. The process of claim 1 wherein said aromatic substrate hydrocarbon comprises benzene, said alkylating agent comprises ethylene, and said second alkyl aromatic hydrocarbon comprises ethylbenzene.

14. The process of claim 1 wherein said aromatic substrate hydrocarbon comprises benzene, said alkylating agent comprises propylene, and said second alkyl aromatic hydrocarbon comprises cumene.

15. The process of claim 1 wherein said transalkylation effluent stream comprises an aromatic selected from the group consisting of a trialkyl aromatic, a tetraalkyl aromatic, a pentaalkyl aromatic, a hexaalkyl aromatic, and a diphenylalkane.

16. The process of claim 1 further characterized in that said alkylation reaction zone operates under at least partial liquid phase conditions.

17. The process of claim 1 further characterized in that said transalkylating occurs at a temperature of from about 250 to about 500° F.

18. The process of claim 1 further characterized in that said transalkylating occurs at a molar ratio of phenyl groups per alkyl group of from about 10:1 to about 1:1.

19. The process of claim 1 further characterized in that said transalkylating occurs at a molar ratio of aromatic substrate per first alkyl aromatic hydrocarbon of from about 13:1 to about 3:1.

20. The process of claim 1 further characterized in that said transalkylation reaction zone operates under at least partial liquid phase conditions.

21. The process of claim 1 further characterized in that said alkylating occurs at a temperature of from about 250 to about 500° F.

22. The process of claim 1 further characterized in that said alkylating occurs at a molar ratio of phenyl groups per alkyl group of from about 5:1 to about 1:1.

23. The process of claim 1 further characterized in that said alkylating occurs at a molar ratio of aromatic substrate per alkylating agent of from about 5:1 to about 1:1.

24. The process of claim 1 wherein said first solid catalyst has a first composition, said second solid catalyst has a second composition, and the first composition and the second composition are the same.

25. The process of claim 1 wherein said transalkylation reaction zone and said alkylation reaction zone are contained in a common vessel.

26. A process for the production of cumene, said process comprising:
   a) contacting an aromatic feed comprising benzene, a benzene recycle stream comprising benzene, and a diisopropylbenzene stream comprising diisopropylbenzene in a transalkylation reaction zone with a transalkylation catalyst at transalkylation conditions to produce a transalkylation zone effluent comprising benzene, cumene, and diisopropylbenzene;
   b) contacting a first aliquot portion of said transalkylation zone effluent and a first olefin feed comprising propylene and propane in an alkylation reaction zone with a solid alkylation catalyst at alkylation conditions to provide an alkylation zone effluent comprising propane, benzene, cumene, diisopropylbenzene, and a heavies hydrocarbon;
   c) passing a second aliquot portion of said transalkylation zone effluent to a benzene separation zone, passing said alkylation zone effluent to said benzene separation zone, separating compounds passed to said benzene separation zone into a benzene fraction comprising benzene and propane and a benzene separation zone bottoms stream comprising cumene, diisopropylbenzene, and said heavies hydrocarbon;
   d) separating said benzene fraction in a light ends column into said benzene recycle stream and a light ends stream comprising propane;
   e) separating said benzene separation zone bottoms stream into a product stream comprising cumene and a heavy bottoms stream comprising diisopropylbenzene and said heavies hydrocarbon; and
   f) separating said heavy bottoms stream into a heavies stream comprising said heavies hydrocarbon that is removed from the process and said diisopropylbenzene stream.

27. A process for the production of ethylbenzene, said process comprising:
   a) contacting an aromatic feed comprising benzene, a benzene recycle stream comprising benzene, and a diethylbenzene stream comprising diethylbenzene in a transalkylation reaction zone with a transalkylation catalyst at transalkylation conditions to produce a transalkylation zone effluent comprising benzene, ethylbenzene, and diethylbenzene;
   b) contacting a first aliquot portion of said transalkylation zone effluent and a first olefin feed comprising ethylene in an alkylation reaction zone with a solid alkylation catalyst at alkylation conditions to provide an alkylation zone effluent comprising light paraffins, benzene, ethylbenzene, diethylbenzene, and a heavies hydrocarbon;
   c) passing a second aliquot portion of said transalkylation zone effluent to a benzene separation zone, passing said alkylation zone effluent to said benzene separation zone, separating compounds passed to in said benzene separation zone into a benzene fraction comprising benzene and light paraffins and a benzene separation zone bottoms stream comprising ethylbenzene, diethylbenzene, and said heavies hydrocarbon;
   d) separating said benzene fraction in a light ends column into said benzene recycle stream and a light ends stream comprising said light paraffins;
   e) separating said benzene separation zone bottoms stream into a product stream comprising ethylbenzene and a heavy bottoms stream comprising diethylbenzene and said heavies hydrocarbon; and
   f) separating said heavy bottoms stream into a heavies stream comprising said heavies hydrocarbon that is removed from the process and said diethylbenzene stream.

* * * * *